US012758691B2

(12) United States Patent
Heselwood et al.

(10) Patent No.: US 12,758,691 B2
(45) Date of Patent: Oct. 13, 2026

(54) BREAST PUMP AND BREAST PUMP VALVE ASSEMBLY

(71) Applicant: Mayborn (UK) Limited, Newcastle upon Tyne (GB)

(72) Inventors: Gerard Heselwood, Newcastle upon Tyne (GB); Matthew James Gossington, Newcastle upon Tyne (GB)

(73) Assignee: Mayborn (UK) Limited, Newcastle upon Tyne (GB)

( * ) Notice: Subject to any disclaimer, the term of this patent is extended or adjusted under 35 U.S.C. 154(b) by 757 days.

(21) Appl. No.: 18/250,479

(22) PCT Filed: Oct. 26, 2021

(86) PCT No.: PCT/GB2021/052787
§ 371 (c)(1),
(2) Date: Apr. 25, 2023

(87) PCT Pub. No.: WO2022/090710
PCT Pub. Date: May 5, 2022

(65) Prior Publication Data

US 2023/0405192 A1 Dec. 21, 2023

(30) Foreign Application Priority Data

Oct. 26, 2020 (GB) ...................................... 2016973

(51) Int. Cl.
*A61M 1/06* (2006.01)
*A61M 39/24* (2006.01)

(52) U.S. Cl.
CPC ............ *A61M 1/062* (2014.02); *A61M 39/24* (2013.01)

(58) Field of Classification Search
CPC ........ A61M 1/062; A61M 39/24; A61M 1/06; A61M 1/1565; A61M 5/14224
See application file for complete search history.

(56) References Cited

U.S. PATENT DOCUMENTS 5,941,847 A * 8/1999 Huber .................. A61M 1/066 604/74
2008/0255503 A1* 10/2008 Quackenbush ....... A61M 1/064 604/74
2020/0139026 A1* 5/2020 O'Toole ................ A61M 1/062

OTHER PUBLICATIONS

PCT Search Report and Written Opinion issued in PCT/GB2021/052787, mailed Feb. 7, 2022 (13 Pages).

(Continued)

*Primary Examiner* — Bradley J Osinski
(74) *Attorney, Agent, or Firm* — Fish & Richardson P.C.

(57) ABSTRACT

The present invention relates to abreast pump, in particular abreast pump and a breast pump valve assembly each for use in providing negative pressure when expressing milk. A breast pump valve assembly comprises a suction chamber for fluid connection to a negative pressure source. A fluid chamber is defined between a first one-way valve and a second one-way valve, wherein the first one-way valve is configured to allow flow of fluid into the fluid chamber and the second one-way valve is configured to allow flow of fluid out of the fluid chamber. A displacement member fluidly separates the suction chamber and the fluid chamber and is configured such that application of negative pressure to the suction chamber causes movement of the displacement member to thereby increase the volume of the fluid chamber and draw fluid into the fluid chamber through the first one-way valve.

28 Claims, 12 Drawing Sheets

(56) References Cited

OTHER PUBLICATIONS

GB Combined Search & Examination Report dated Apr. 22, 2021 (5 pages).
GB Combined Search & Examination Report dated Mar. 3, 2022 (7 pages).
GB Examination Report dated Nov. 9, 2022 (5 pages).

* cited by examiner

BREAST PUMP AND BREAST PUMP VALVE ASSEMBLY

The present invention relates to a breast pump, in particular a breast pump and a breast pump valve assembly each for use in expressing milk.

INTRODUCTION

Breast pumps, commonly used by mothers to express breast milk, generally include a breast receiving part, also known as a breast shield or horn, for receiving the breast and nipple, and a pump to generate and apply suction. The breast receiving part is shaped so that a surface can contact the breast and form an air-tight seal against the skin to ensure suction is applied to the nipple within the breast receiving part.

Suction, also known as vacuum pressure, vacuum or negative pressure, is provided by a negative pressure source, such as a manual or electrical pump. Manual breast pumps require the user to manually actuate a membrane or piston using a handle mounted to or on the breast receiving part. Electric breast pumps use an electrically-powered pump unit which is either mounted to the breast receiving part, or is remote therefrom and is fluidly connected to the breast receiving part by vacuum tubing and connectors.

Suction generated by both manual and electrical pumps is provided in pulses causing suction to be applied to the nipple in cycles. The suction stimulates expression of breastmilk from the nipple which flows away from the breast receiving part and is collected in a suitable container arranged in fluid communication.

A one-way valve is provided between the breast receiving part and the container to control breastmilk flowing into the container while preventing suction from the pump being applied to the container. Within one suction cycle, the pump generates a suction pulse within the breast receiving part, before releasing or venting the suction to atmospheric pressure so that expressed breastmilk is able pass through the one-way valve to the container. Subsequent cycles repeat the pulse and release process. In manual pumps, the rate and intensity of each cycle is controlled by the user whereas electrical pumps are electronically controlled using either pre-programmed or manually adjusted settings.

A known problem of such breast pumps is that pumping is inefficient due to the release of suction after each cycle, which necessitates repeatedly generating suction from atmospheric pressure within the breast receiving part. A further drawback is that release of suction causes stimulation of the nipple to cease, slowing the overall rate of milk expression. A yet further drawback is that the release of suction can cause the air-tight seal between the breast receiving part and the breast to fail, leading to leaks and requiring the user to maintain the positioning of the breast pump against the breast by applying pressure, which causes discomfort.

A further problem of known breast pumps is that they require large pump devices able to pump large volumes of air. This requires the pump to be either a separate, remote pump or, if integrated with the breast receiving part, adds considerable weight and bulk to the breast receiving part.

It is therefore an object of the invention to provide a breast pump with improved efficiency. In particular, it is an object of the present invention to provide a breast pump which provides efficient suction and which improves the rate of breastmilk expression. It is a further object of the present invention to provide a breast pump with improved comfort and reduced leaks for the user.

SUMMARY OF THE INVENTION

According to a first aspect of the invention, there is provided a breast pump valve assembly including:

- a suction chamber for fluid connection to a negative pressure source;
- a fluid chamber defined between a first one-way valve and a second one-way valve, wherein the first one-way valve is configured to allow flow of fluid into the fluid chamber and the second one-way valve is configured to allow flow of fluid out of the fluid chamber; and
- a displacement member fluidly separating the suction chamber and the fluid chamber, wherein the displacement member is configured such that application of negative pressure to the suction chamber causes movement of the displacement member to thereby increase the volume of the fluid chamber and draw fluid into the fluid chamber through the first one-way valve.

Suitably, the displacement member is configured such that, when pressure in the suction chamber is equal to or greater than pressure in the fluid chamber, the displacement member moves to thereby decrease the volume of the fluid chamber and direct fluid in the fluid chamber through the second one-way valve.

Suitably, the displacement member is configured to move towards the vacuum port upon application of negative pressure to the suction chamber.

Suitably, the displacement member is configured to move between a neutral position when the suction chamber is at atmospheric pressure, and a displaced position when the suction chamber is under negative pressure. Suitably, in the neutral position, the displacement member substantially closes at least a portion of the fluid chamber.

Suitably, the displacement member and first and second one-way valves are integrally formed.

Suitably, the displacement member comprises a flexible diaphragm configured to deform upon application of negative pressure to the suction chamber.

Suitably, at least one of the displacement member and first and second one-way valves are formed from a fluid impermeable flexible material.

Suitably, the flexible material has a Shore A hardness of 30 to 70 Shore A. In one example, the flexible material has a Shore A hardness of 50 Shore A.

Suitably, the displacement member comprises a reciprocating member biased towards the fluid flow path.

Suitably, at least one of the first and second one-way valves is a duck bill valve.

Suitably, the breast pump valve assembly further includes a housing having an upper (first) member defining the fluid chamber, and a lower (second) member defining the suction chamber. Suitably, the displacement member is positioned between the upper and lower portion of the housing. Suitably, the upper portion of the housing is releasably coupled to the lower portion of the housing.

Suitably, the breast pump valve assembly further includes a fluid inlet, wherein the first one-way valve is configured to allow flow of fluid from the fluid inlet to the fluid chamber. Suitably, the valve assembly further includes an inlet port for fluidly coupling the inlet to a breast receiving part of a breast pump.

Suitably the first housing member is configured as a lid for coupling to the opening of a fluid container. Suitably, the first housing member comprises a fluid outlet configured to allow flow of fluid from the second one-way valve directly into a fluid container.

Suitably, the valve assembly further includes a fluid outlet, wherein the second one-way valve is configured to allow flow of fluid from the fluid chamber to the outlet. Suitably, the valve assembly further includes an outlet port for fluidly coupling the outlet to a fluid collection container.

According to a second aspect of the invention there is provided a breast pump valve assembly including:

a variable volume fluid chamber defined between a first one-way valve and a second one-way valve, wherein the first one-way valve is configured to allow flow of fluid into the fluid chamber and the second one-way valve is configured to allow flow of fluid out of the fluid chamber; and a displacement member configured for varying the volume of the fluid chamber, wherein the displacement member is configured such that movement of the displacement member to increase the volume of the fluid chamber thereby draws fluid into the fluid chamber through the first one-way valve.

Suitably, the valve assembly further includes a suction chamber, wherein the displacement member fluidly separates the suction chamber and the fluid chamber.

Suitably, the valve assembly further comprise a vacuum port for fluidly connecting the suction chamber to a negative pressure source.

Suitably, the displacement member is configured such that application of negative pressure to the suction chamber causes movement of the displacement member to thereby increase the volume of the fluid chamber and draw fluid through the first one-way valve into the fluid chamber.

Suitably, the valve assembly further comprises an actuator configured to enable manual movement of the displacement member to thereby vary the volume of the fluid chamber.

According to a third aspect of the invention, there is provided a breast pump including:

a suction chamber and a vacuum port for fluidly connecting the suction chamber to a negative pressure source;

a breast receiving part, a fluid collection container, and a fluid flow path extending between the breast receiving part and the fluid collection container;

a fluid chamber defined between a first one-way valve and a second one-way valve in the fluid flow path, wherein the first one-way valve is configured to allow flow of fluid from the breast receiving part into the fluid chamber, and the second one-way valve is configured to allow flow of fluid from the fluid chamber to the fluid collection container; and a displacement member fluidly separating the suction chamber and the fluid chamber, wherein the displacement member is configured such that application of negative pressure to the suction chamber causes movement of the displacement member to thereby increase the volume of the fluid chamber and draw fluid from the breast receiving part through the first one-way valve into the fluid chamber.

Suitably, the displacement member is configured such that, increase of pressure in the suction chamber towards atmospheric pressure causes movement of the displacement member to thereby decrease the volume of the fluid chamber and direct fluid in the fluid chamber through the second one-way valve to the fluid collection container.

Suitably, the breast pump further includes a negative pressure source fluidly connected to the vacuum port. Suitably, the negative pressure source is one of: a piezoelectric pump, a diaphragm pump, a reciprocating pump, or a peristaltic pump.

It will be appreciated that any of the features described above in relation to the first aspect of the invention may apply equally to the second and third aspects of the invention.

Certain aspects of the invention provide a breast pump valve assembly enabling improved efficiency compared to known breast pumps.

Certain aspects of the invention provide a breast pump valve assembly providing improved user comfort compared to known breast pumps.

BRIEF DESCRIPTION OF THE DRAWINGS

Embodiments of the invention are now described, by way of example only, with reference to the accompanying drawings, in which.

In the drawings, like reference numerals refer to like parts.

DETAILED DESCRIPTION

Figure 1:
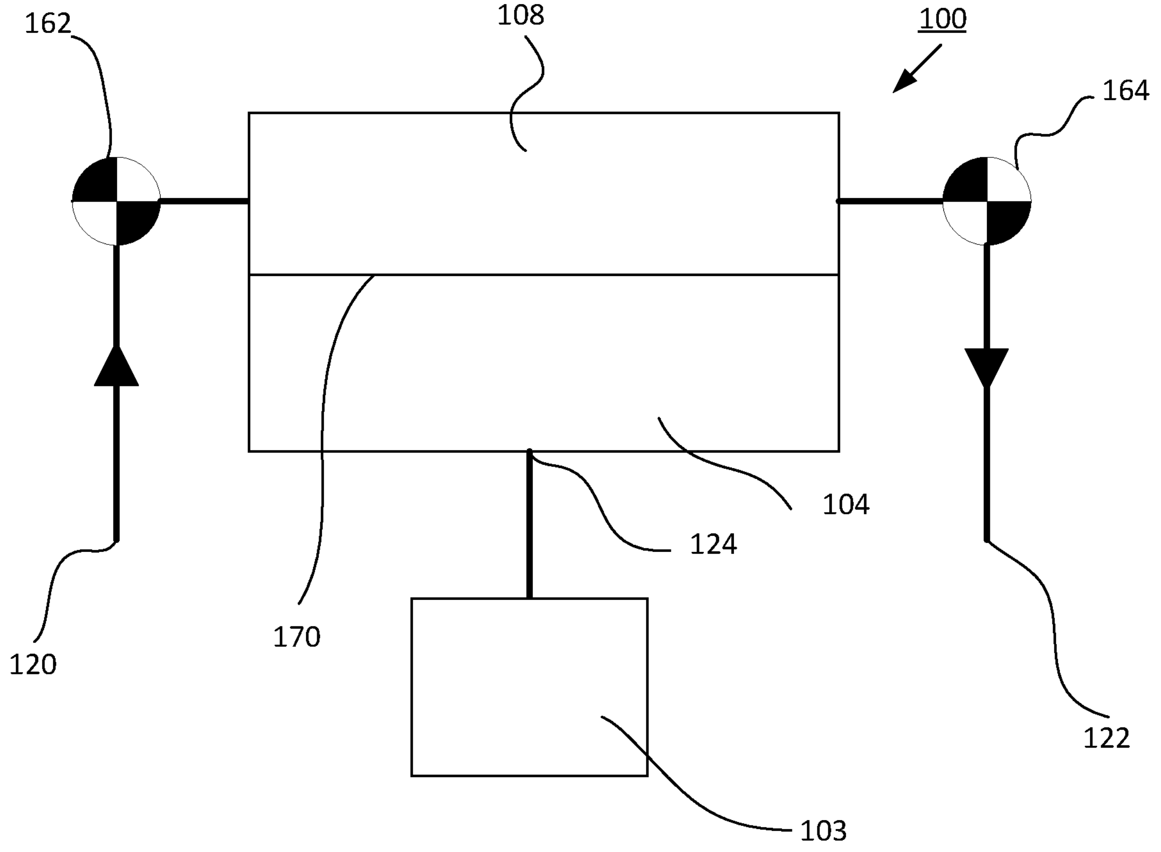
FIG. 1 shows a schematic of a first example breast pump valve assembly.

Certain terminology is used in the following description for convenience only and is not limiting. The words ‘lower’ and ‘upper’ designate directions in the drawings to which reference is made and are with respect to the described component when assembled and mounted. The words ‘inner’, ‘inwardly’ and ‘outer’, ‘outwardly’ refer to directions toward and away from, respectively, a designated centreline or a geometric centre of an element being described (e.g. central axis), the particular meaning being readily apparent from the context of the description.

Further, unless otherwise specified, the use of ordinal adjectives, such as, 'first', 'second' etc. merely indicate that different instances of like objects are being referred to and are not intended to imply that the objects so described must be in a given sequence, either temporally, spatially, in ranking or in any other manner.

Referring now to FIG. 1, there is shown a schematic of a breast pump valve assembly 100 including a suction chamber 104, for fluid connection to a negative pressure source 103, and a fluid chamber 108 defined between a first one-way valve 162 and a second one-way valve 164. The first one-way valve 162 is configured to allow fluid to flow into the fluid chamber 108. The second one-way valve 164 is configured to allow fluid to flow out of the fluid chamber 108.

The valve assembly 100 further includes a displacement member 170, arranged to fluidly separate the suction chamber 104 from the fluid chamber 108. The displacement member 170 is configured such that application of negative pressure to the suction chamber 104 causes the displacement member 170 to move and thereby increase the volume of fluid chamber 108, drawing fluid (e.g. breast milk) into the fluid chamber 108 through the first one-way valve 162.

As the pressure in the suction chamber 104 becomes equal to or greater than a pressure in the fluid chamber 108, the displacement member 170 moves to decrease the volume of the fluid chamber 108. As such, fluid in the fluid chamber 108 is directed out of the fluid chamber 108 through the second one-way valve 164, e.g. towards a fluid collection container (not shown).

The displacement member 170 is aptly configured to assume a neutral position when the pressure in the suction chamber 104 is substantially equal to the pressure in fluid chamber 108. For example, the displacement member 170 may assume the neutral position when the suction chamber 104 is substantially at atmospheric pressure. The displacement member 170 may then move to a displaced position when the suction chamber is under negative pressure.

The suction chamber 104 may aptly include a vacuum port 124 configured for fluid connection to the negative pressure source 103. The vacuum port 124 may aptly be positioned such that the displacement member 170 moves towards the vacuum port 124 upon application of negative pressure to the suction chamber 104. For example, the vacuum port 124 may be positioned in a portion of the suction chamber 104 opposite the displacement member 170.

In the neutral position, the displacement member 170 may be configured to substantially close at least a portion of the fluid chamber 108, for example by abutting against an opposite wall of the fluid chamber 108. In this way, in the neutral position a substantial portion of or substantially all fluid may be removed from the fluid chamber 108 via the second one-way valve 164.

The valve assembly further includes a fluid inlet 120 and a fluid outlet 122. The first one-way valve 162 is configured to allow flow of fluid from the fluid inlet 120 into the fluid chamber 108. In this example, the first one-way valve 162 is positioned between the fluid inlet 120 and the fluid chamber 108.

The second one-way valve 164 is configured to allow flow of fluid from the fluid chamber 108 to the fluid outlet 122. In this example, the second one-way valve is positioned between the fluid chamber 108 and the fluid outlet 122.

FIGS. 2 to 5 show a first example configuration of the valve assembly 100 of FIG. 1. In this example, the valve assembly 100 includes a housing having a first housing member 130 and a second housing member 110. In this example, the first housing member is an upper member 130 and the second housing member is a lower member 110. The upper member 130 generally defines the fluid chamber 108. The lower member 110 generally defines the suction chamber 104. The displacement member 170 is positioned in between the upper member 130 and the lower member 110, thereby fluidly separating the suction chamber 104 and the fluid chamber 108.

In this example, the lower member 110 includes a first opening, defining the fluid inlet 120, a second opening, defining the fluid outlet 122, and a third opening, defining the vacuum port 124. In other examples, one or more of the openings may be provided in another portion of the housing, for example one or more openings may be provided in the upper member 130.

In this example, the lower member 110 is provided as a plate having upper and lower (or inner and outer) surfaces 111, 112. The lower member 110 includes first and second end portions 114, 116 separated by a centre portion 118. The centre portion 118 includes a recess 119 on the upper surface 111. In this example, the recess 119 is circular, though it will be appreciated that other shapes may be suitable.

The first opening, defining the fluid inlet 120, is provided through the first end portion 114 and the second opening, defining the fluid outlet 122, is provided through the second, opposing end portion 116. The third opening, defining the vacuum port 124, is provided in the recess 119. In this example the vacuum port 124 is provided at the centre of the circular recess 119. The fluid inlet 120, fluid outlet 122 and vacuum port may aptly be arranged along a lengthways axis of the lower member 110.

The inlet 120 may aptly include an inlet port for fluidly coupling the inlet to a breast receiving part of a breast pump. In this example the inlet port includes a tube extending through the first end portion 114. In this example the tube extends from the upper surface 111, through the first end portion 114 to the lower surface 112 and further extends away from, and normal to, the lower surface 112. The inlet port may directly extend to the breast receiving part of a breast pump or may couple to a tube extending between and providing fluid communication between the inlet port and the breast receiving part.

The outlet 122 may aptly include an outlet port for fluidly coupling the outlet to a fluid collection container. In this example, the outlet port includes a connector 126 on the lower surface 112 of the lower member 110. The connector 126 extends around the fluid outlet 122 and is configured for attachment to tubing or other fluid pathways extending to a fluid collection container. In this example, the connector 126 is substantially elongate and extends along a portion of the lower surface 112 (i.e. parallel to the lower surface 112).

The vacuum port 124 is configured for fluid connection to a vacuum source or source of negative pressure (e.g. a pump). The vacuum port 124 may include a tube extending from the upper surface 111, through the centre portion 118 of the lower member 110, and away from the lower surface 112 to an outer tube section 125. In this example, the outer tube section 125 is arranged to extend parallel to the outer surface 112 in a direction forming a locus between the inlet 120 and outlet 122. The outer tube section 125 may be directly connected to a vacuum source or may be connected to a vacuum tube connected at a distal end to a vacuum source.

In this example, the upper member 130 is provided as a plate having upper and lower (or outer and inner) surfaces 131, 132. The upper member 130 includes first and second end portions 134, 136, separated by a centre portion 138. The centre portion 138 includes a cavity (or recess) 137 on the lower surface 132. The cavity 137 defines at least a portion of the fluid chamber 108 between the first one-way valve 162 and second one-way valve 164. In this example, the cavity 137 is circular and includes first and second concentric annular channels 140, 141. However, it will be appreciated that other cavity shapes may also be suitable.

Figure 3:
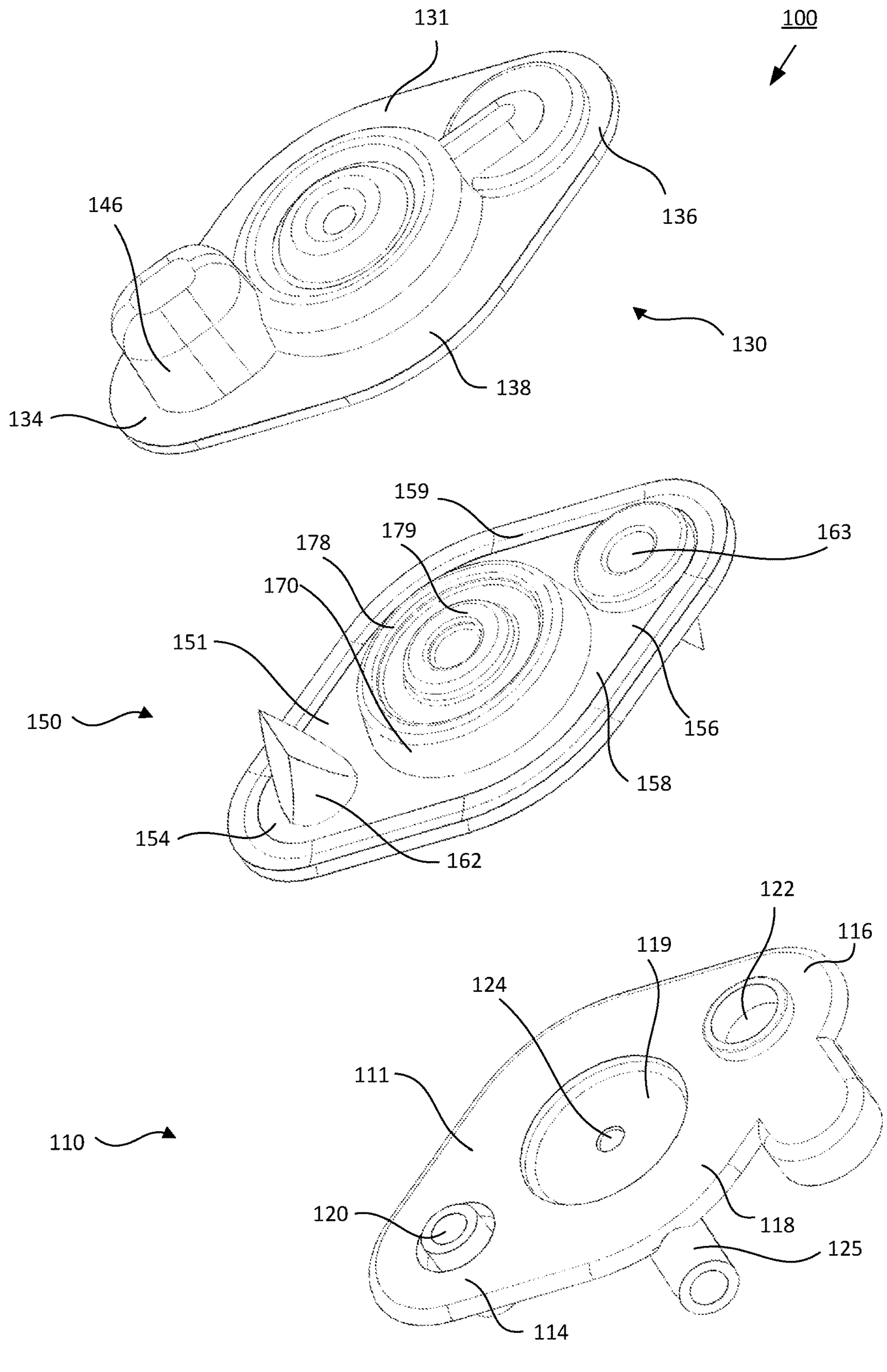
FIG. 3 shows an exploded perspective view from above of the components of the breast pump valve assembly of FIG. 2.

A recess 144 is provided in the lower surface 132 of the first end portion 134. The recess 144 is sized and shaped to house the first one-way valve 162 (as shown in FIG. 3). The recess 144 is aptly circular and is accommodated within the internal cavity of a boss 146 which projects away from the upper surface 131 of the first end portion 134.

In this example, a support member 150 is positioned between the upper member 130 and the lower member 110. The support member 150 includes the displacement member 170, the first one-way valve 162 and the second one-way valve 164. In this way, the displacement member 170, and first and second one-way valves 162, 164 are integrally formed.

The support member 150 includes a first surface 151 facing the upper member 130 and a second surface 152 facing the lower member. The support member 150 is sized and shaped to correspond to the shape of the upper member 130 and lower member 110.

In this example, the support member 150 includes first and second end portions 154, 156, separated by a centre portion 158. An edge portion 159 extends around the support member 150 enclosing the first and second end portions 154, 156 and the centre portion 158. The edge portion 159 may aptly form a thickened outer rim portion, which may be clamped between the inner surface 132 of the upper member 130 and the inner surface 111 of the lower member 110.

The support member 150 includes a first opening 161 extending through the first end portion 154. The first opening 161 is configured to align with the fluid inlet 120. The first opening 161 is provided with the first one-way valve 162, adapted to selectively allow fluid to pass through the first opening 161.

In this example, the first one-way valve 162 is a duck bill valve including a pair of mutually-opposed inclined walls, extending from the first surface 151 of the displacement member 150, angled to meet at a first ridge parallel to and distal from the first surface 151.

A slit is provided along and through the first ridge, adapted to move between open and closed positions in response to pressure differences across the mutually-opposed inclined walls, as is known in the art. In this way, the first one-way valve 162 is configured to allow fluid to pass through the first opening 161 in a direction from the second surface 152 to the first surface 151, while preventing fluid passing through in a reverse direction.

The support member 150 includes a second opening 163 extending through the second end portion 156. The second opening 163 is configured to align with the fluid outlet 122. The second opening 163 is provided with the second one-way valve 164, adapted to selectively allow fluid to pass through the second opening 163.

In this example, the second one-way valve 164 is a duck bill valve including a pair of mutually-opposed inclined walls, extending from the second surface 152 of the support member 150. The second one-way valve 164 allows fluid to pass through the second opening 163 in a direction from the first surface 151 to the second surface 152, while preventing fluid passing through in a reverse direction.

The support member 150 further includes the displacement member 170, which in this example is a flexible diaphragm. The flexible diaphragm 170 is configured to deform upon application of negative pressure to the suction chamber 104.

The diaphragm 170 is positioned such that it aligns with the recess 119 on the lower member 110 and the cavity 137 in the upper member 136. In this way, the diaphragm 170 is configured to fluidly separate the recess 119 (forming the suction chamber 104) and the cavity 137 (forming at least part of the fluid chamber 108).

In this example, the support member 150 includes an inner rim 182, which may be a thickened region. The inner rim 182 extends around the periphery of the diaphragm 170. The inner rim 182 may be clamped between the inner surface 132 of the upper member 130 and the inner surface 111 of the lower member 110. In this way, the inner rim 182 may help to form a fluid seal over the recess 119 to form the suction chamber 104.

The diaphragm 170 may aptly be shaped to correspond to the cavity 137 in the upper member 130. In this way, in the neutral position the diaphragm may abut against an inner surface of the cavity, thereby minimizing the volume of the fluid chamber 108 as much as possible and ensuring substantially all fluid can be expelled therefrom.

For example, the diaphragm 170 may be provided in the centre portion 158 of the support member 150. The diaphragm 170 may include a base 172, recessed from the second surface 152 by an angled wall 174 extending around the base 172. The base 172 may be circular and include a pair of recessed annular grooves 176, 177 arranged concentrically with the angled wall 174. The recessed annular grooves 176, 177 form corresponding annular projections 178, 179 on the first side of the displacement member 150 which are sized and profiled to match the concentric annular channels 140, 141 of the upper member 130 centre portion 138. In this way, deformation of the diaphragm 170 is provided by deformation of the diaphragm annular wall 174, as well as the annular grooves 176, 177 and the base 172.

In this example, the first and second one-way valves 162, 164 and the diaphragm 170 are arranged along a lengthways axis of the support member 150. The first and second one-way valve 162, 164 and the diaphragm 170 are integrally formed on the support member 150.

Features of the support member 150 are configured to engage with corresponding features of the upper and lower members 110, 130. Engagement of the corresponding features provides a number of volumes within the housing volume, as is described below, with particular reference to FIG. 4.

The upper member 130 and the lower member 110 are configured to be releasably coupled to thereby form a complete housing with the support member 150 positioned in between. The upper member 110 and the lower member 130 are each formed as a single part having a substantially common footprint and adapted to releasably couple together in order to form the complete housing. For example, each of the upper member 110 and the lower member may include cooperating features enabling them to releasably clip together.

The outer rim portion 159 and inner rim portion 182 of the support member 150 are shaped to be clamped between the upper and lower members 130, 110 when coupled to form the housing. When clamped, the support member 150 divides the housing to form the fluid chamber 108 between the support member 150 and the upper member 130 and the suction chamber 104 between the displacement member 170 of the support member 150 and the lower member 110.

Figure 4:
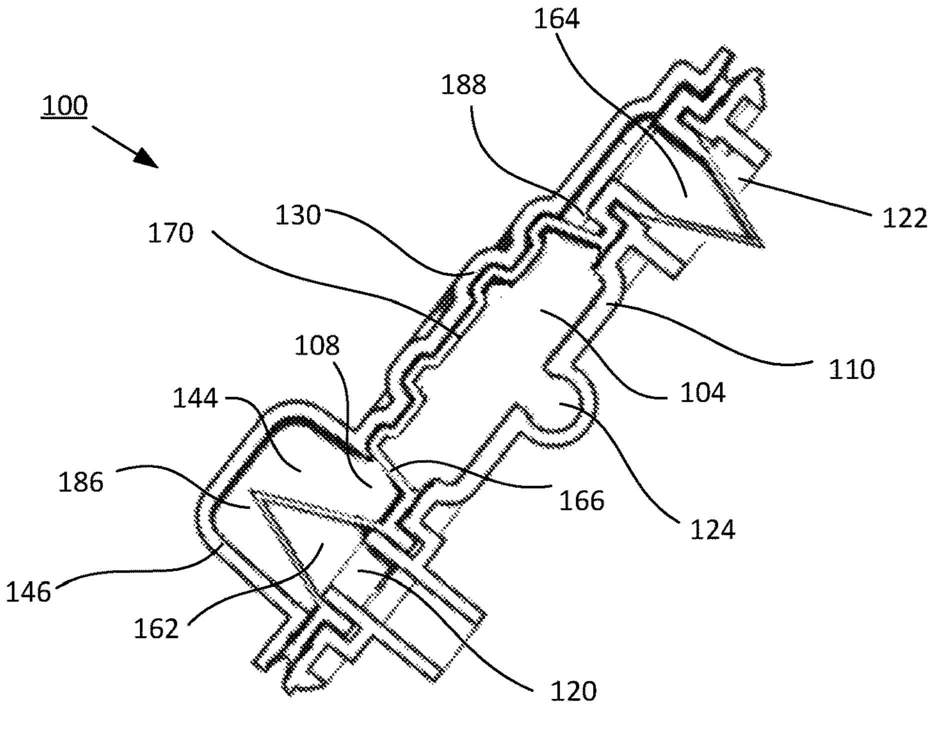
FIG. 4 shows a cross-sectional view of the breast pump valve assembly of FIG. 2.
Figure 5:
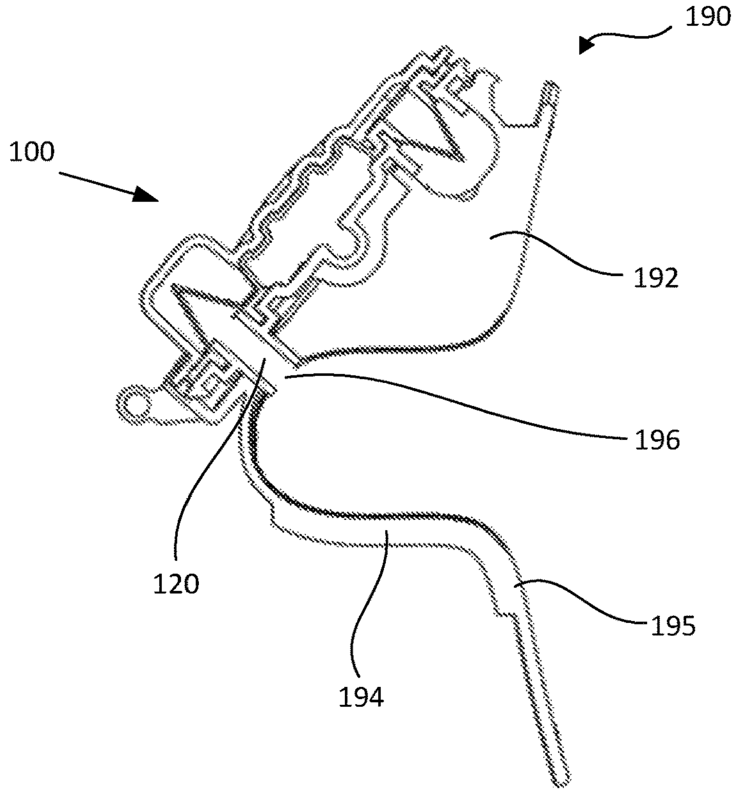
FIG. 5 shows a cross-sectional view of a breast pump including the breast pump valve assembly of FIG. 2.

Referring now to FIG. 4, there is shown a cross-sectional view of the assembled breast pump valve assembly 100 of the first example. The first surface 151 of the support member 150 is oriented to engage the lower (inner) surface 132 of the upper member 130. The second surface 152 of the support member 150 is oriented to engage the upper surface 111 of the lower member 110.

The outer rim 159 and inner rim 182 of the support member 150 is clamped between respective portions of the upper and lower members 130, 110 so that the support member 150 is sandwiched within the housing. As the entire outer rim 159 is clamped to form a fluid seal, the lower surface 132 of the upper member 130 is fluidly isolated from the upper surface 111 of the lower member 110. The first surface 151 of the support member 150 is fluidly isolated from its second surface 152.

In the assembled configuration, the first one-way valve 162 is fluidly coupled to the fluid inlet 120, and the second one-way valve 164 is fluidly coupled to the fluid outlet. In this way a single fluid flow path is formed from the fluid inlet 120, through the first one-way valve 162, along the fluid chamber 108, through the second one-way valve 164 to the fluid outlet 122.

In this example, the first end portion 154 of the support member 150 is positioned intermediate the respective first end portions 134, 114 of the upper and lower members 130, 110. The first opening 161 of the support member 150 is mounted to the fluid inlet 120 on the lower member upper surface 111, oriented so that the inclined walls of the first one-way valve 162 extend away from the fluid inlet 120. In this way, the first one-way valve 162 caps the inlet 120 and selectively allows fluid into the housing from the fluid inlet 120.

The second end portion 156 of the support member 150 is positioned intermediate the respective second end portions 136, 116 of the upper and lower members 130, 110. The second opening 163 of the support member 150 is mounted to the fluid outlet 122 on the lower member inner surface 111, and oriented so that the inclined walls of the second one-way valve 164 extend into the fluid outlet 122. In this way, the second one-way valve 164 caps the outlet 122 and selectively allows fluid to leave the housing through the fluid outlet 122.

The centre portion 158 of the support member 150 is positioned intermediate the respective centre portions 138, 118 of the upper and lower members 130, 110. The diaphragm 170 of the support member 150 is mounted above the circular recess 119 of the lower member inner surface 112, oriented so that the second surface 152 faces the circular recess 119. The diaphragm 170 abuts the upper member lower surface 132, oriented so that the annular projections 178, 179 on the support member 150 are received within the concentric annular channels 140, 141 of the upper member 130.

With the support member 150 positioned within the housing, the housing volume is divided into two chambers. The suction chamber 104 is provided by the volume defined between the diaphragm 170 and the recess 119, delimited by the abutment between the inner rim 182 of the support member and the inner surface 111 of the lower member 110 around the recess 119.

The fluid chamber 108 is provided by the volume defined between the upper member 130 and the first side 151 of the support member 150, delimited by the clamping of the outer rim portion 159 between the upper member 130 and lower member 110.

In this example, the diaphragm 170 abuts the upper housing lower surface 132 so that the fluid chamber 108 is sub-divided into first and second compartments 186, 188 with a closed portion provided in between. The first compartment is in fluid communication the first one-way valve 162. The second compartment is in fluid communication with the second one-way valve 164. In this configuration, the diaphragm 170 is in the neutral position.

The diaphragm 170 remains in the neutral position as long as there are equal pressures in the fluid chamber 108 and suction chamber 104. In the neutral position the volume of the fluid chamber 108 is minimized and the volume of the suction chamber 104 is maximized. As such, with the diaphragm in the neutral position, substantially all of the fluid may be expelled from the fluid chamber 108 via the second one-way valve 164.

The diaphragm 170 is configured to respond to negative pressure provided to the suction chamber 104. In use, negative pressure may be introduced to the suction chamber 104 via the vacuum port 124, using any suitable negative pressure source, for example a manual or electric pump. The negative pressure source may provide pulses or cycles of negative pressure, as known in the art.

Within a first cycle, application of negative pressure within the suction chamber 104 deforms the diaphragm 170 to thereby decrease the volume of the suction chamber 104 and expand the volume of the fluid chamber 108.

In this example, upon application of negative pressure to the suction chamber 104, the diaphragm 170 moves away from the centre portion 138 of the upper member 130 to fluidly connect the first and second compartments 186, 188. The volume of the fluid chamber 108 is thereby increased.

As the volume of the fluid chamber 108 increases, the pressure in the fluid chamber 108 decreases, thereby creating a pressure differential across the first one-way valve 162. Due to the pressure differential, the first one-way valve 162 opens to draw fluid from the fluid inlet 120 into the fluid chamber 108.

As negative pressure increases, the diaphragm 170 further deforms, moving further away from the centre portion 138 of the upper housing 130. Negative pressure in the suction chamber 104 increases until the first cycle reaches a maximum negative pressure. At the maximum negative pressure, the diaphragm 170 is in a displaced position. In the displaced position, the volume of fluid chamber 108 is at a maximum and the volume of the suction chamber 104 is at a minimum.

To complete the first cycle, negative pressure in the suction chamber 104 is released, allowing the diaphragm 170 to return to its undeformed neutral shape. The diaphragm 170 therefore moves back to its neutral position in which a portion of the fluid chamber 108 is substantially closed. In this example, in the neutral position, the base 172 of the diaphragm 170 abuts the upper housing 130 inner surface 131. The fluid chamber 108 thus contracts to its minimal volume, in which the fluid chamber 108 is subdivided into first and second compartments with a closed portion provided in between.

Figure 2:
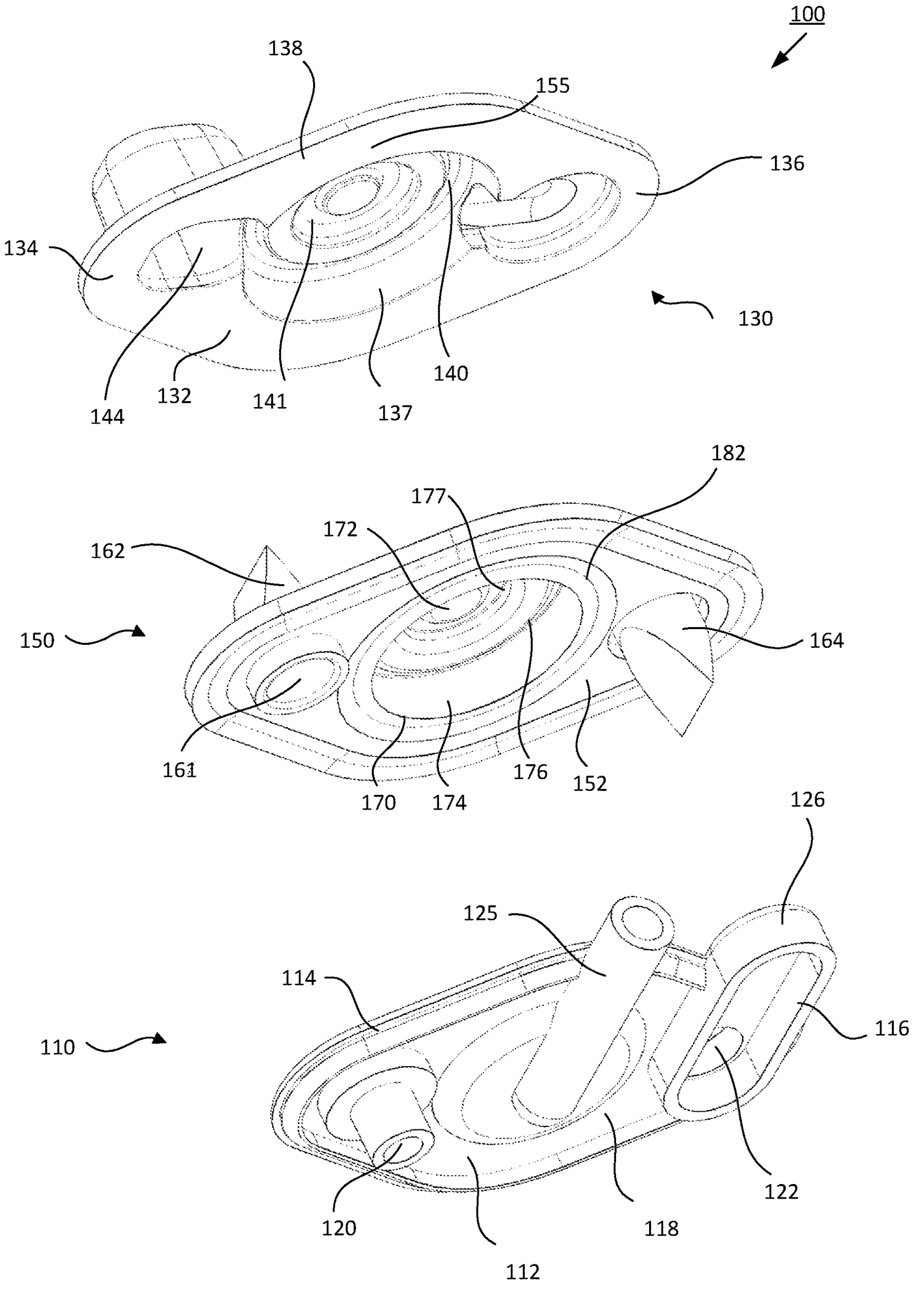
FIG. 2 shows an exploded perspective view from below of the components of the breast pump valve assembly according to a first configuration of the first example.

In the example shown in FIGS. 2 to 4, the upper and lower members 110, 130 are formed from a rigid material, for example a plastic such as polypropylene. Polypropylene (PP) may be particularly advantageous since it is food contact safe, suitable for sterilisation and is inert to cleaning chemicals. In some examples, the upper and lower member may be formed from a filled PP, for example PP+$CaCO_3$, to provide greater strength.

The support member 150 including the diaphragm 170 and first and second one-way valves 162, 164 is formed from a fluid impermeable flexible material. The material is aptly resiliently deformable. For example, suitable materials may include an elastomeric polymer such as silicone rubber. The material may aptly have a Shore A hardness of 30 to 70 Shore A, or aptly 50 Shore A.

Referring now to FIG. 4, there is shown a breast pump 190 suitable for use expressing breastmilk, including the valve assembly 100 of the example shown in FIGS. 2 to 4.

The breast pump 190 further includes a breast receiving part 192 (for example a breast horn), a fluid collection container (not shown) and a fluid flow path extending between the breast receiving part 192 and the fluid collection container. The fluid flow path extends through the valve assembly 100, with the first and second one-way valves 162, 164 disposed in the fluid flow path. The valve assembly 100 is configured substantially the same as the valve assembly 100 described above with the fluid chamber 108 defined between the first and second one-way valves 162, 164.

As such, the first one-way valve 162 is configured to allow flow of fluid (e.g. breast milk) from the breast receiving part 192 into the fluid chamber 108 and the second one-way valve 164 is configured to allow flow of fluid (e.g. breast milk) from the fluid chamber 108 to the fluid collection container. In this way, the fluid flow path is provided from the nipple receiving portion 194 to the fluid collection container via the fluid chamber 108 of the valve assembly.

The breast receiving part 192 includes a nipple receiving portion 194 and a breast contacting portion 195 configured to engage with a user's breast. The nipple receiving portion 194 is provided as a substantially cylindrical cup, suitably sized to receive a user's nipple. The breast contacting portion 192 is provided as a substantially spherical dome, suitably sized to contact the skin around a user's nipple when the nipple is placed inside the nipple receiving portion 194. A first end of the nipple receiving portion 194 opens to the centre of the breast contacting portion 192 to thereby receive the nipple. A second end of the nipple receiving portion 194 includes an opening 196 adapted to allow fluid, such as air or expressed milk, to flow out therefrom.

As described above, the valve assembly 100 includes the suction chamber 104 and the vacuum port 124. The vacuum port 124 of the valve assembly 100 is fluidly connected to a negative pressure source, for example a reciprocating vacuum pump.

The breast pump 190 may include the negative pressure source, or in other examples an external negative pressure source may be used, which can be fluidly coupled to the suction chamber via the vacuum port 124.

The fluid inlet 120 of the valve assembly 100 is fluidly connected to the nipple receiving portion 194, e.g. via the inlet port. In other examples the fluid inlet 120 may be in direct fluid communication or integrally formed with the nipple receiving portion 194.

The fluid outlet 122 is fluidly connected to the fluid collection container. The fluid collection container may be releasably connected to the remaining components of the breast pump 190. For example, the fluid collection container may be releasably connected to the outlet 122 of the valve assembly 100.

To use the breast pump 190, the user places the breast horn 192 against their breast so that their nipple is received within the nipple receiving portion 194. The nipple is received until the breast contacting portion 192 engages with the skin around the nipple, forming a substantially air-tight seal around the open end of the nipple receiving portion 194.

The user activates the negative pressure source so that a first negative pressure cycle commences. As negative pressure increases in the suction chamber 104, the diaphragm 170 deforms from its initial neutral position towards its displaced position, expanding the fluid chamber 108, and thereby generating a negative pressure in the fluid chamber 108. The negative pressure in the fluid chamber 108 provides a pressure difference across the first one-way valve 162 allowing it to open and draw fluid from the nipple receiving portion 194 and applying negative pressure to the user's nipple, stimulating expression of breast milk.

Fluid, including expressed breast milk, is drawn into the valve assembly 100 from the nipple receiving portion 194 by the negative pressure of fluid chamber 108. As the diaphragm 170 reaches its displaced position, negative pressure in the suction chamber 104 is released, allowing the pressure in the suction chamber 104 to return towards atmospheric pressure, and thereby allowing the diaphragm to return to its neutral position.

The initial pressure release in the suction chamber 104 causes the diaphragm 170 to return towards its undeformed shape. The diaphragm 170 thus moves towards to its neutral position, thereby decreasing the volume of the fluid chamber 108 and causing the diaphragm 170 to apply increased pressure to any fluid within the fluid chamber 108. The increased pressure closes the first one-way valve 162, and opens the second one-way valve 164. With the first one-way valve 162 closed, backflow of fluid to the nipple receiving portion 194 is prevented. With the second one-way valve 164 opened, fluid is expelled from the fluid chamber 108 through the outlet 122. Fluid is directed from through the outlet 122 to the fluid collecting chamber as the diaphragm 170 returns to its neutral position. When the negative pressure in the suction chamber 104 reaches atmospheric pressure, first the cycle is complete and a subsequent pressure cycle may commence.

In the above described cycle, closure of the first one-way valve 162 fluidly isolates the nipple receiving portion 194 from the fluid chamber 108, meaning a residual negative pressure remains within the nipple receiving portion 194 as the diaphragm 170 moves from the displaced position to the neutral position. Thus, during the release part of the negative pressure cycle, a residual negative pressure is maintained within the nipple receiving portion 194. This helps to retain the seal between the breast receiving portion 195 and the breast and also helps to provide continuous stimulation of the nipple to ensure expression of breast milk continues for the duration of the negative pressure cycle.

So long as the seal between the breast receiving portion 195 and the skin is maintained, stimulated expression of milk may be maintained by residual negative pressure in the nipple receiving portion 194, even without a subsequent negative pressure cycle. Furthermore, at the commencement of a subsequent negative pressure cycle the residual negative pressure within the nipple receiving portion 194 means that the negative pressure source is not required to evacuate fluid from the nipple receiving portion 194 in order provide further stimulation. Stimulated expression of breastmilk is provided in a continuous, efficient manner without interruption.

Figure 6:
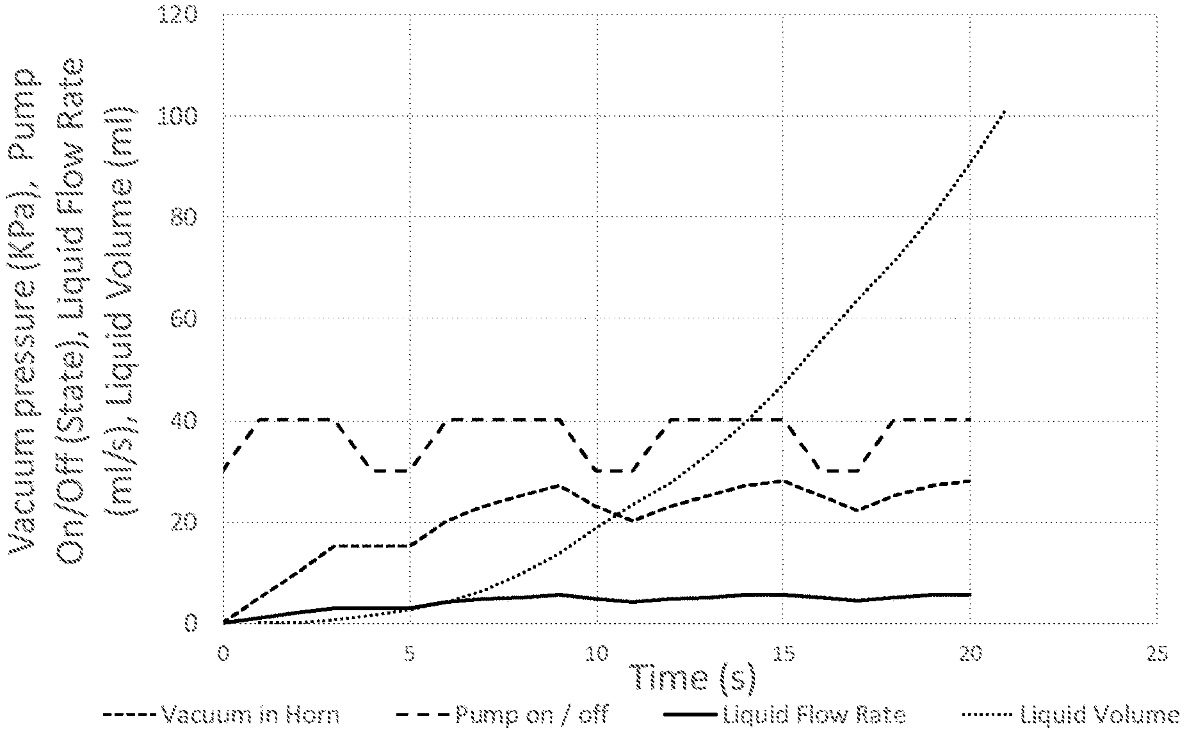
FIG. 6 shows the pressure and liquid flow in the breast pump over the pump cycle.

This effect is illustrated more clearly in FIG. 6, which illustrates the pump cycle over time. As shown, after just two pump cycles, the vacuum in the horn (the nipple receiving portion 194) is maintained at a steady pressure, whilst the liquid flow rate stays continuous through the cycle. This enables the collected liquid volume to increase at a steady rate over time.

Figure 7:
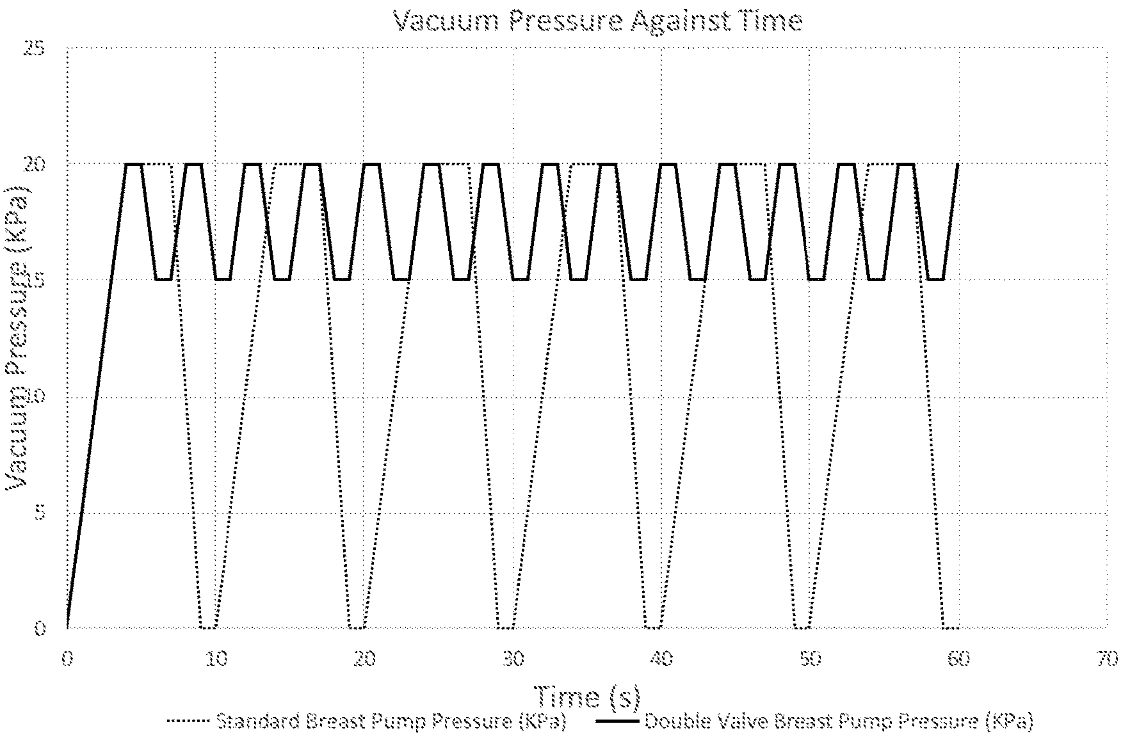
FIG. 7 compares the pressure at the nipple over the pump cycle of the present invention with that of a single valve prior art pump.

FIG. 7 illustrates the pressure at the nipple receiving portion over time for the present invention (double valve breast pump) and a known standard breast pump including a single valve. As shown, the present invention enables a constant steadily fluctuating negative pressure to be maintained at the nipple. This helps to hold the breast receiving part in place against the breast, thereby reducing movement of the breast pump when in use, and in turn reducing the probability of leaks. The area under the graph represents work being done. It is clear that in the present invention the work is continuous, thereby enabling constant extraction of milk and increased efficiency. Comfort to the user may also be improved due the reduced fluctuations in pressure at the nipple.

Figure 8:
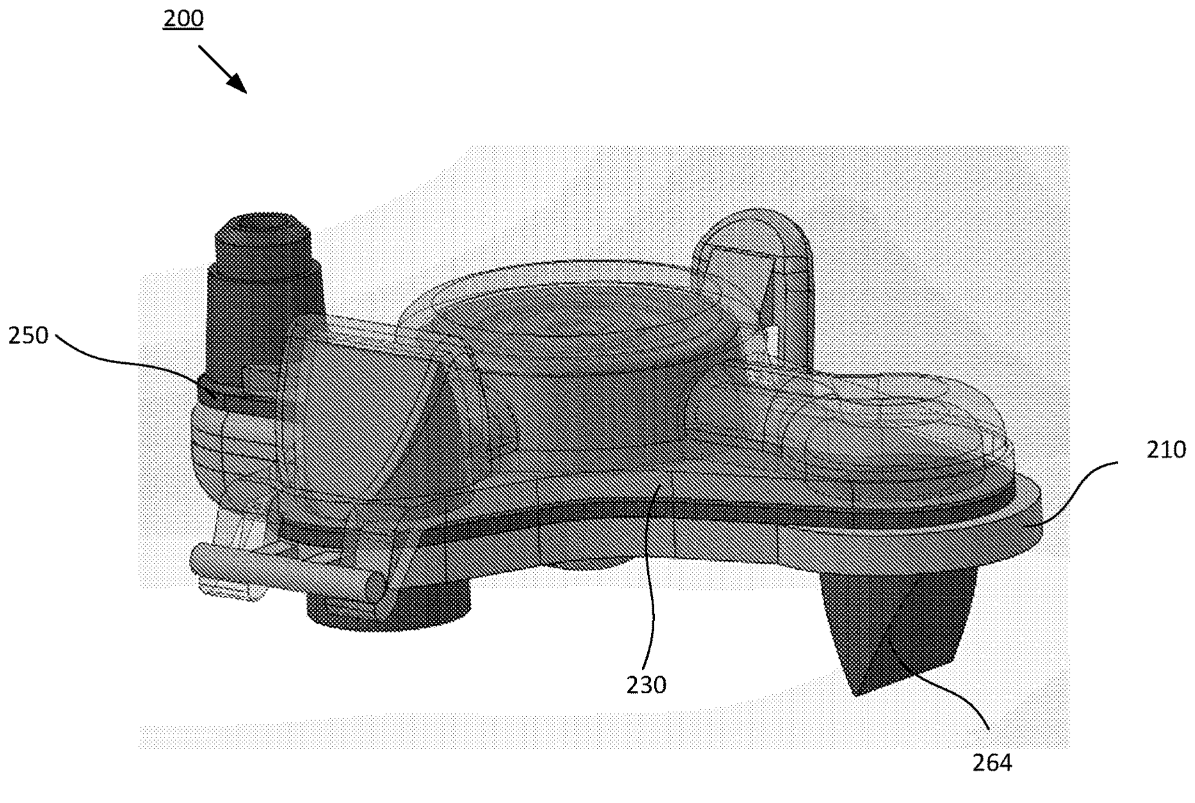
FIG. 8 shows a perspective view of a breast pump valve assembly according to a second example.
Figure 9A:
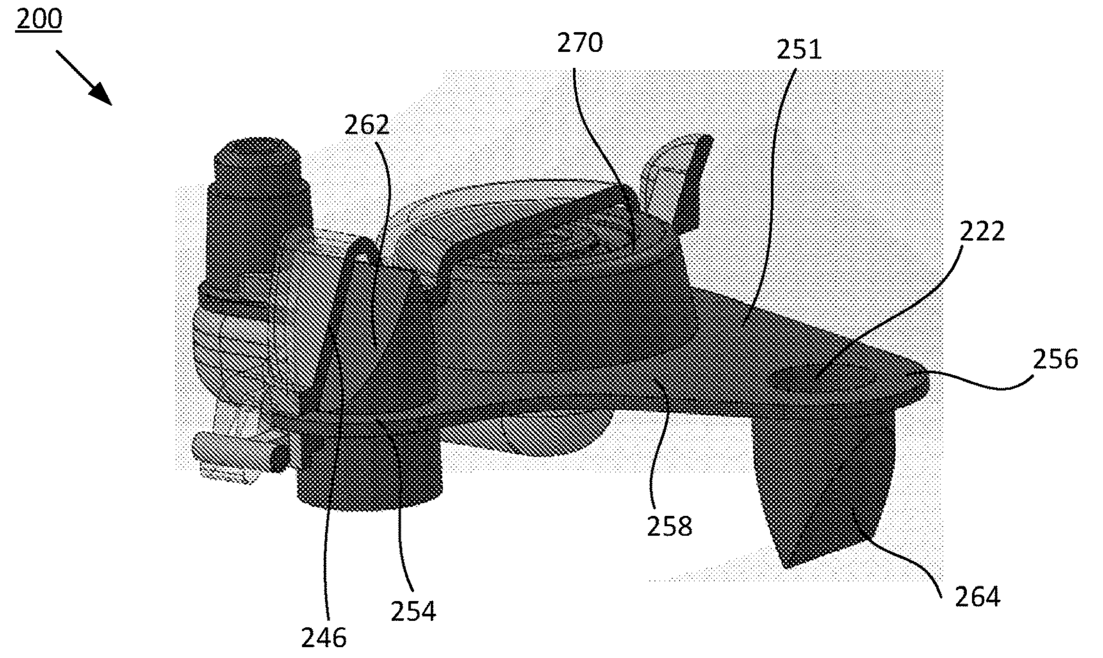
FIG. 9 shows cut-away perspective views from (a) above and (b) below of the second example.
Figure 9B:
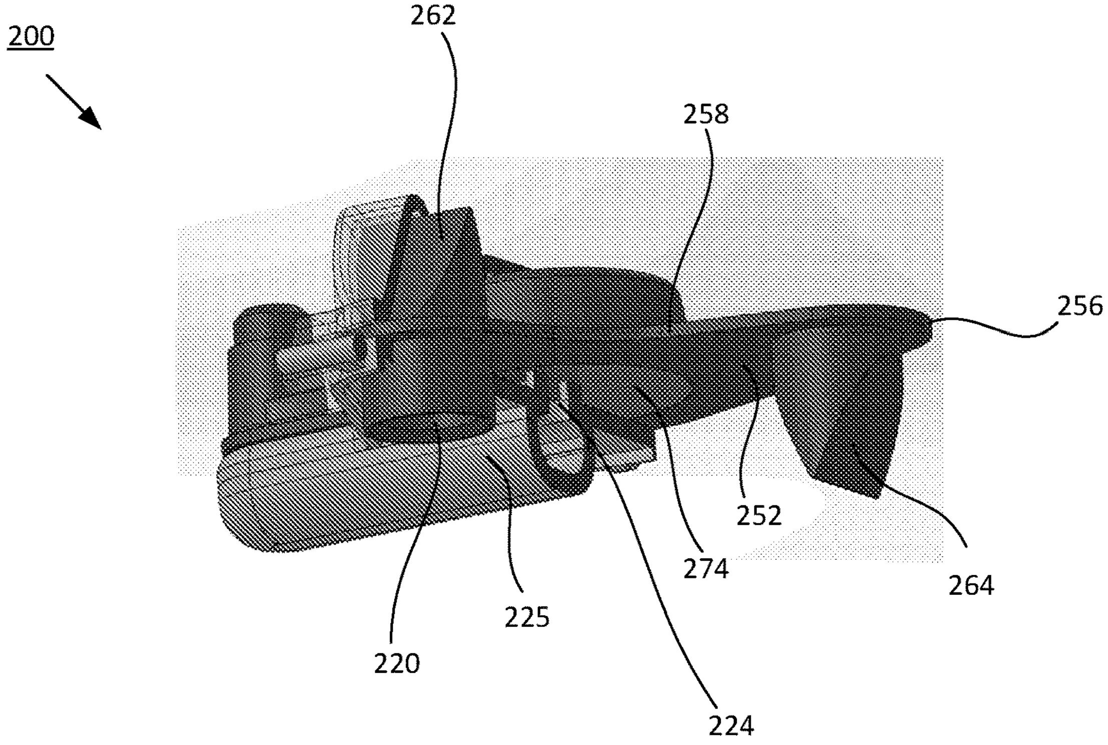
Figure 10:
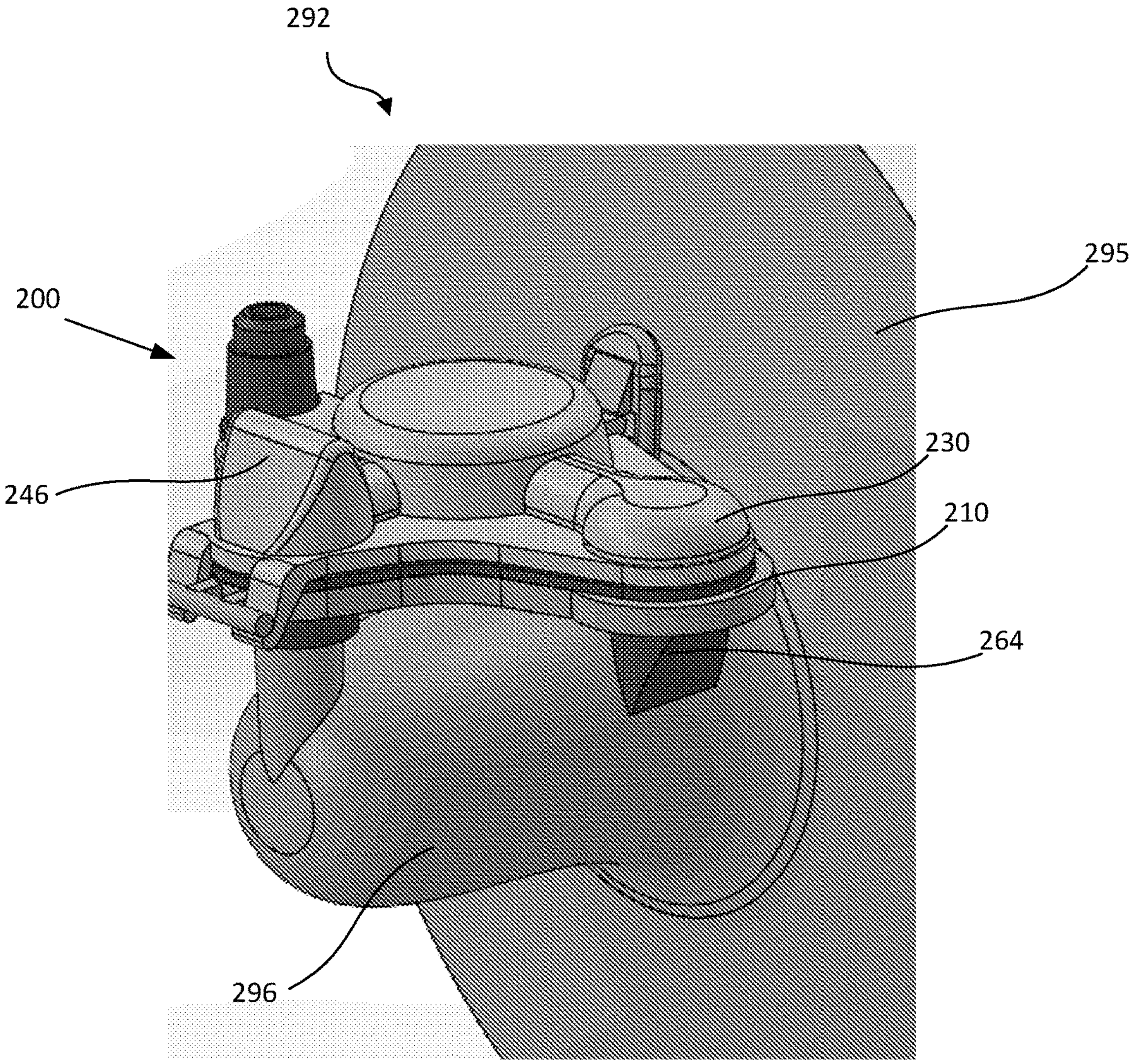
FIG. 10 shows a perspective view of second example mounted to a breast receiving part.

Referring now to FIGS. 8 to 10, there is shown a second example breast pump valve assembly 200. Where the features are the same as the first example, the reference numbers are the same other than the initial digit is a “2”. The example shown in FIGS. 8 to 10 is similar to the example shown in FIGS. 1 to 5, such that the assembly 200 includes a suction chamber and fluid chamber defined between a first one-way valve 262 and a second one-way valve 264. The valve assembly 200 further includes a displacement member 270, arranged to fluidly separate the suction chamber from the fluid chamber, configured such that application of negative pressure causes the displacement member 270 to move and thereby increase the volume of fluid chamber, drawing liquid into the fluid chamber through the first one-way valve 262.

The valve assembly 200 includes a housing which includes an upper member 230 and a lower member 210, and a support member 250 positioned in between. In contrast to the first example, the lower member 210 is provided as an L-shaped plate having upper and lower surfaces.

The lower member 210 includes first and second end portions arranged orthogonally around a centre portion. A fluid inlet 220 is provided through the first end portion, a fluid outlet 222 is provided through the second end portion and a vacuum port 224 is provided through the centre portion. The fluid inlet 220 and the vacuum port 224 are arranged along a first axis, and the fluid outlet 222 and the vacuum port are arranged along a second axis arranged perpendicular to the first axis.

The upper member 230 is provided as an L-shaped plate having upper and lower surfaces. The upper member 230 includes first and second end portions, arranged orthogonally around a centre portion. The upper member 230 further includes a recess 246 configured to house the first one-way valve 262. A cavity is provided on the lower surface of the centre portion.

The support member 250 is provided as an L-shaped sheet having first and second surfaces 251, 252 and including first and second end portions 254, 256, arranged orthogonally around a centre portion 258. An edge portion extends around the support member 250 enclosing the first and second end portions 254, 256 and the centre portion 258.

A first opening extends through the first end portion 254 of the support member 250 and includes a first one-way valve 262, which in this example is a duckbill valve. A second opening extends through the second end portion 256 and includes a second one-way valve 264, which in this example is a duckbill valve. The centre portion 258 includes a diaphragm 270 which includes the same features as the diaphragm 170 of the first example.

The upper member 210, lower member 230 and support member 250 couple and assemble in substantially the same manner as described above with reference to FIGS. 1 to 4.

Referring now to FIG. 10, there is shown the valve assembly 200 mounted to a breast horn 292. The breast horn 292 includes a nipple receiving portion 296 and a breast contacting portion 295 shaped and configured to engage with a user’s breast in the same manner as the breast horn 192 of FIG. 5. A first end of the nipple receiving portion 294 includes an opening adapted to allow fluid, such as air or expressed milk, to flow out therefrom.

The valve assembly 200 and breast horn may be included in a breast pump, not shown, including a negative pressure source, to be used in the same manner as breast pump 290 described above.

Figure 12:
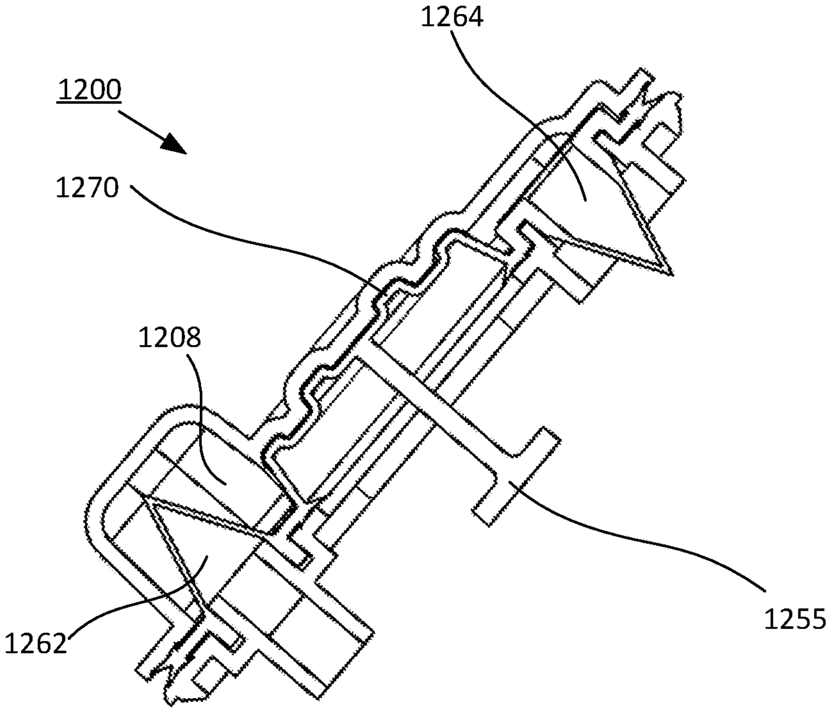
FIG. 12 shows another example of a breast pump valve assembly.
Figure 13:
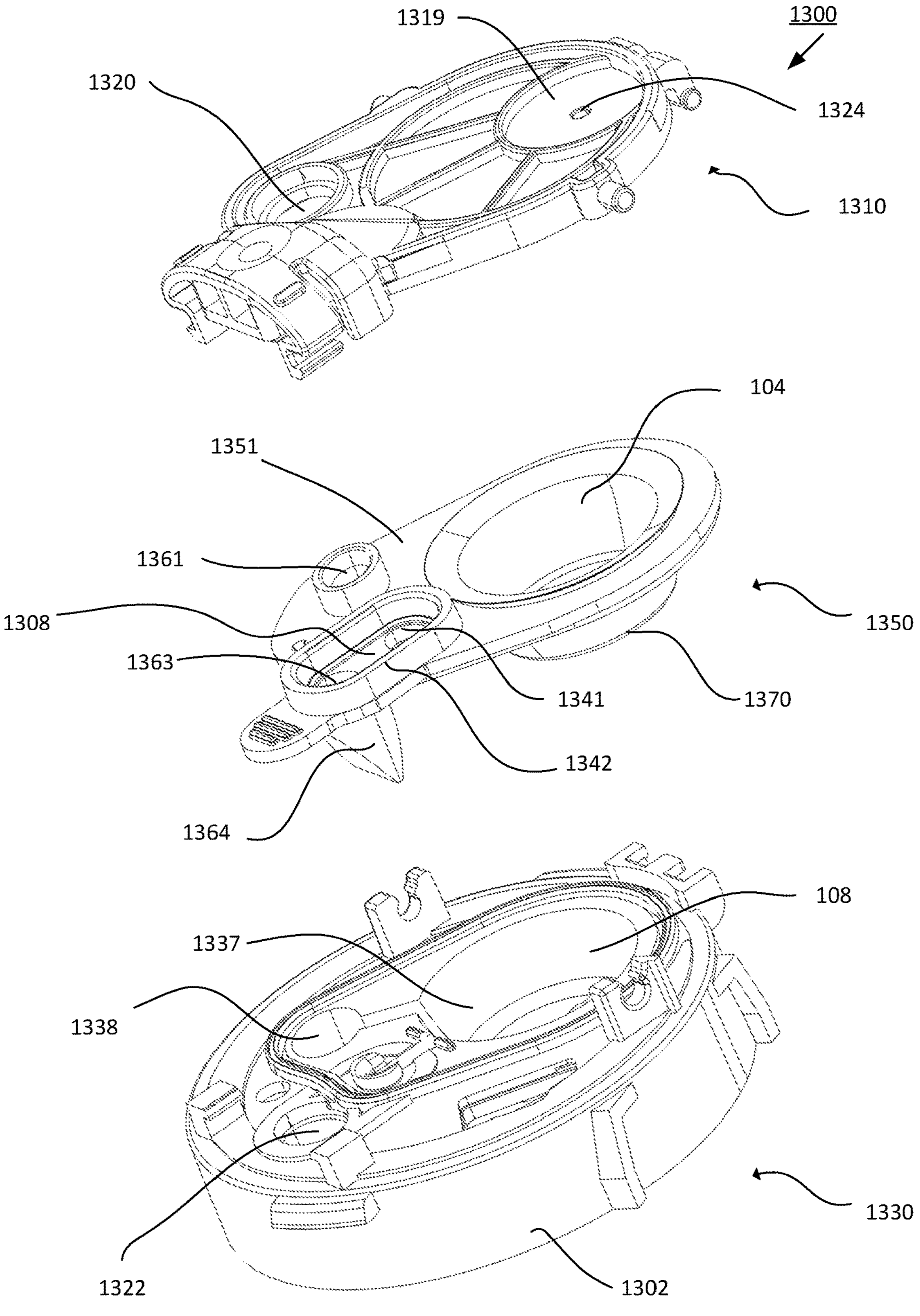
FIG. 13 shows an exploded view of another breast pump valve assembly.

In a further example, as shown in the valve assembly 1200 of FIG. 12, the suction chamber may be omitted and the displacement member may be configured to vary the volume of the fluid chamber by a mechanical means rather than by use of negative pressure. Where the features are the same as the first example, the reference numbers are the same other than the initial digit is a “12”. For example, the valve assembly 1200 may include a variable volume fluid chamber 1208 defined between a first one-way valve 1262 and a second one-way valve 1264 similar to the examples described above.

The first one-way valve 1262 is configured to allow flow of fluid into the variable volume fluid chamber 1208, and the second one-way valve 1264 is configured to allow flow of fluid out of the variable volume fluid chamber 1208.

Similar to the examples described above, the valve assembly 1200 includes a displacement member 1270 that is configured to vary the volume of the fluid chamber 1208. Movement of the displacement member 1270 to increase the volume of the fluid chamber 1208 thereby draws fluid into the fluid chamber 1208 through the first one-way valve 1264. Similar to the examples described above, movement of the displacement member 1270 to decrease the volume of the fluid chamber 1208 thereby expels fluid from the fluid chamber 1208 through the second one-way valve 1264.

In this example, movement of the displacement member 1270 may be effected by any suitable means. For example, the valve assembly may further comprise an actuator 1255 configured to operably move the displacement member 1270 to thereby vary the volume of the fluid chamber 1208. The actuator 1255 may be in the form of a lever that the user can move in order to move the displacement member. The actuator may be controlled either manually or by an electric motor, for example, in order to move the displacement member 1270.

The remaining components of the valve assembly 1200 may be formed according to any of the examples described herein.

FIGS. 13 to 16 show another example configuration of the valve assembly 100 of FIG. 1. In this example, the valve assembly 1300 includes a housing having a first housing member 1330 and a second housing member 1310. The second housing member is an upper member 1310 and the first housing member is a lower member 1330. The lower member 1330 generally defines the fluid chamber 108. The upper member 1310 generally defines the suction chamber 104. The displacement member 1370 is positioned in between the upper member 1310 and the lower member 1330, thereby fluidly separating the suction chamber 104 and the fluid chamber 108.

In this example, the upper member 1310 includes a first opening, defining the fluid inlet 1320, and a second opening, defining the vacuum port 1324. The vacuum port 1319 may be fluidly coupled to any suitable vacuum source as described herein.

The fluid inlet 1320 may aptly include an inlet port for fluidly coupling the inlet to a breast receiving part of a breast pump.

The lower member 1330 includes an opening, defining a fluid outlet 1322. In this example, the lower member 1330 is configured as a lid for coupling to an opening of a fluid collection container (not shown). Whilst various lid configurations may be possible, in this example the lower member includes an annular wall 1302 including a threaded radially inner surface (not shown). In this way, the lower member 1330 may be directly coupled to the open neck of a fluid collection container, via a threaded interface to form a fluid tight coupling. This configuration allows fluid to pass directly from the fluid outlet 1322 into a fluid collection container, without the need for intermediate fluid pathways or tubing, which may be difficult for a user to clean.

In this example, the lower member 1330 includes a cavity 1337, which defines at least a portion of the fluid chamber 108 between the first one-way valve 1362 and second one-way valve 1364. In this example, the cavity 1337 is circular in cross-section. However, it will be appreciated that other cavity shapes may also be suitable.

In this example, a support member 1350 is positioned between the upper member 1310 and the lower member 1330. The support member 1350 includes the displacement member 1370, the first one-way valve 1362 and the second one-way valve 1364. In this way, the displacement member 1370, and first and second one-way valves 1362, 1364 are integrally formed.

The support member 1350 includes a first surface 1351 facing the upper member 1310 and a second surface 1352 facing the lower member 1330. The support member 1350 includes a first opening 1361 configured to align with the fluid inlet 1320 in the upper member 1310. The first opening 1361 is provided with the first one-way valve 1362, adapted to selectively allow fluid to pass through the first opening 1361 into the fluid chamber 108.

In this example, the first one-way valve 1362 (see FIG. 16) is a duck bill valve extending from the second surface 1352 of the displacement member 1350. The duck bill valve functions the same as other duck bill valves described herein.

The support member 1350 includes a second opening 1363 configured to align with the fluid outlet 1322 in the lower member 1330. The second opening 1363 is provided with the second one-way valve 1364, adapted to selectively allow fluid to pass through the fluid outlet 1322.

In this example, the second one-way valve 1364 is a duck bill valve extending from the second surface 1352 of the support member 1350. The duck bill valve functions the same as other duck bill valves described herein. In this example, both the first and second one-way valves extend in the same direction. This allows for a more compact valve assembly, which may be particularly beneficial in wearable breast pumps, for example, to reduce overall size of the pump.

The support member 1350 further includes the displacement member 1370, which in this example is a flexible diaphragm. The flexible diaphragm 1370 is configured to deform upon application of negative pressure to the suction chamber 104.

The diaphragm 1370 is positioned such that it aligns with the cavity 1337 in the lower member 1330 and the vacuum port 1324 in the upper member 1310. In this way, the diaphragm 1370 is configured to fluidly separate the suction chamber 104, which is defined between the diaphragm 1370 and the upper member 1310, and the fluid chamber 108, which is defined between the cavity 1337 and the diaphragm 1370. The upper member 1310 includes an annular seal ring or abutment ring 1312, configured to provide a fluid tight seal around a rim of the diaphragm 1370. In this way, a substantially fluid tight suction chamber 104 is provided between the upper member 1310 and the diaphragm 1370.

The diaphragm 1370 may aptly be shaped to correspond to the cavity 1337 in the lower member 1330. In this way, in the neutral position the diaphragm may abut against an inner surface of the cavity, thereby minimizing the volume of the fluid chamber 108 as much as possible and ensuring substantially all fluid can be expelled therefrom.

Features of the support member 1350 are configured to engage with corresponding features of the upper and lower members 1310, 1330

The upper member 1310 and the lower member 1330 are configured to be releasably coupled to thereby form a complete valve housing with the support member 1350 positioned in between. The upper member 1310 and the lower member 1330 are each adapted to releasably couple together in order to form the complete housing. For example, each of the upper member 110 and the lower member may include cooperating features enabling them to releasably clip together.

An outer rim portion 1359 and inner rim portion 1382 of the support member 1350 are shaped to be clamped between the upper and lower members 1310, 1330 when coupled to form the housing. When clamped, the support member 1350 divides the housing to form a primary fluid chamber 108 between the support member 1350 and the upper member 1310 and the suction chamber 104 between the displacement member 1370 and the lower member 1330.

Figure 14:
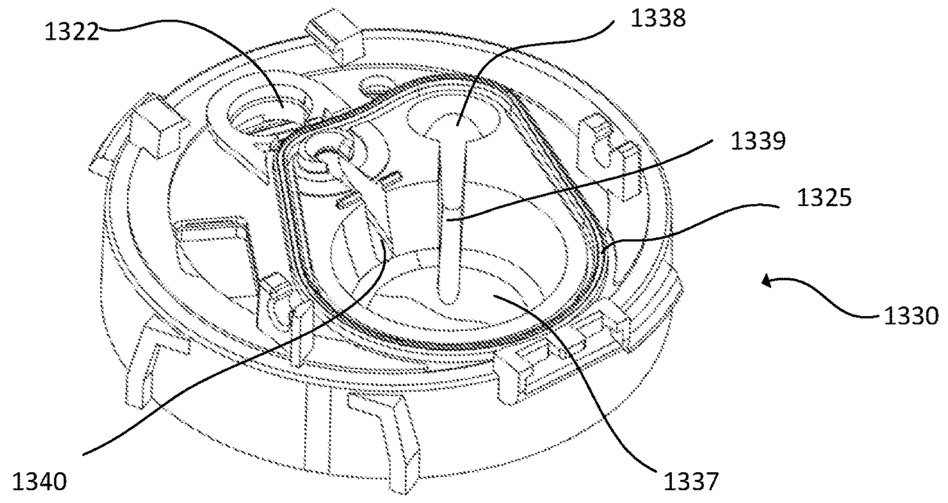
FIG. 14 shows the lower member of the breast pump valve assembly of FIG. 13.
Figure 15:
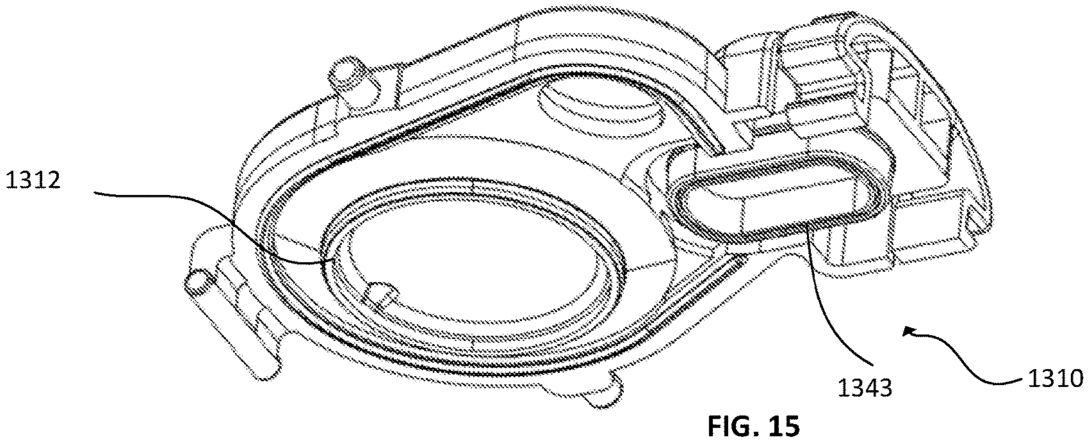
FIG. 15 shows the underside of the upper member of the breast pump valve assembly of FIG. 13.
Figure 16:
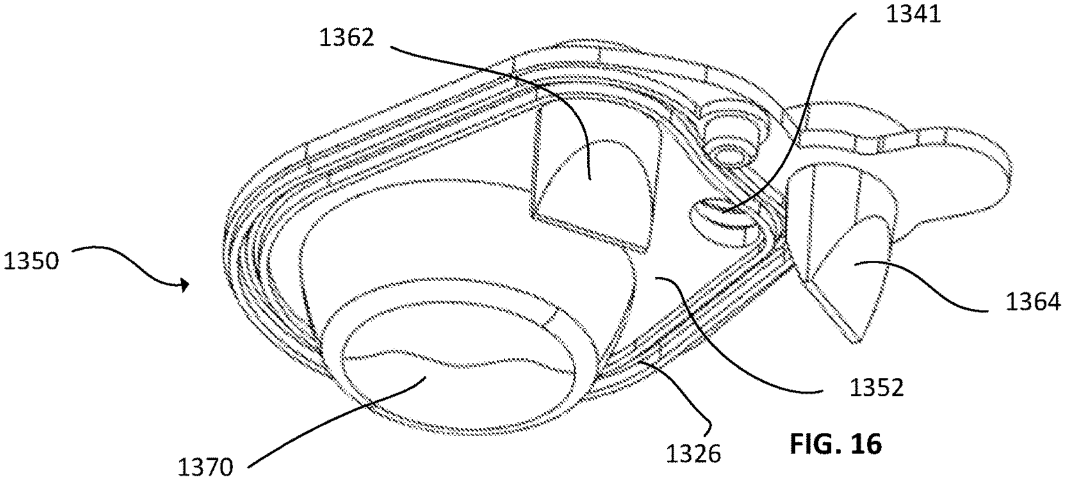
FIG. 16 shows the underside of the support member of the breast pump valve assembly of FIG. 13.

FIG. 14 illustrates a detailed perspective view of the lower member 1330, showing the fluid cavity 1337 and flow channels in further detail. The lower member 1330 includes a first fluid well 1338. The first fluid well 1338 is configured to align with and accommodate at least a portion of the fluid inlet valve 1362 of the support member 1350. As such, in use, fluid enters into the fluid well 1338 from the fluid inlet valve 1362.

The lower member 1330 further includes a first fluid flow channel 1339 extending from the fluid well 1338 to the fluid cavity 1337. In this way, the fluid well 1338 is fluidly coupled to the fluid cavity 1337 via the first fluid flow channel 1339. A second fluid flow channel 1340 extends from the fluid cavity 1337 towards the fluid outlet 1322.

In this example, the fluid outlet 1322 is configured to align with and accommodate the fluid outlet valve 1364, with the fluid outlet valve 1364 extending in the same direction as the fluid inlet valve 1362. As such, the support member 1310 and the lower member 1352 are configured to direct fluid upwardly from the fluid cavity 1337, through a fluid aperture 1341 in the support member 1350, and then through the fluid outlet valve 1364 and the fluid outlet 1322. In this example, the second fluid flow channel 1340 is inclined from the base of the cavity 1337 towards to the aperture 1341 in the support member 1350 to help aid flow of fluid towards and through the aperture 1341.

The lower member includes a sealing abutment or seal ring 1325 extending around the fluid cavity 1337, the fluid well 1338 and the first and second fluid flow channels 1339, 1340. The sealing abutment or seal ring 1325 is configured to provide a fluid seal against the second surface 1352 of the support member 1350. As such the primary fluid chamber 108 is defined between the support member 1350 and the lower member 1330.

In this example the support member 1350 includes a channel 1326 on the second surface 1352. The channel 1326 encircles displacement member 1370, the fluid inlet valve 1362 and the fluid aperture 1341 and is configured to receive the sealing abutment or seal ring 1325 of the lower member 1330 to provide a fluid seal. It will be appreciated that in some examples, the channel 1326 may be omitted and a suitable fluid seal may be provided by abutment of the seal ring 1325 against the second surface 1352 of the support member 1350.

The support member 1350 further includes an annular wall 1342 extending from the first surface 1351 and encircling the aperture 1341 and the second opening 1363. The annular wall 1341 is configured to seal against the upper member 1310, thereby forming a secondary fluid chamber 1308 defined between the support member and the upper member in the region within the annular wall 1341.

In this example, the upper member 1310 includes a projection 1343 configured to sealingly abut against the annular wall 1342. However, it will be appreciated that the projection 1343, may be omitted and the fluid seal may be provided by abutment of the annular wall directly against the underside of the upper member 1310.

In use, as the diaphragm 1370 is displaced (by a suitable vacuum source) towards the upper member 1310, fluid (i.e. breast milk) is pulled into the primary fluid chamber 108 via the first one-way valve 1362, into the fluid well 1338 and along the first fluid flow channel 1339 into the fluid cavity 1337. As the diaphragm 1370 returns to the neutral position, fluid is expelled from the primary fluid chamber 108, through the aperture 1341 into the secondary fluid chamber 1308 and out through the second one-way valve 1364 into a fluid collection container.

Figure 17:
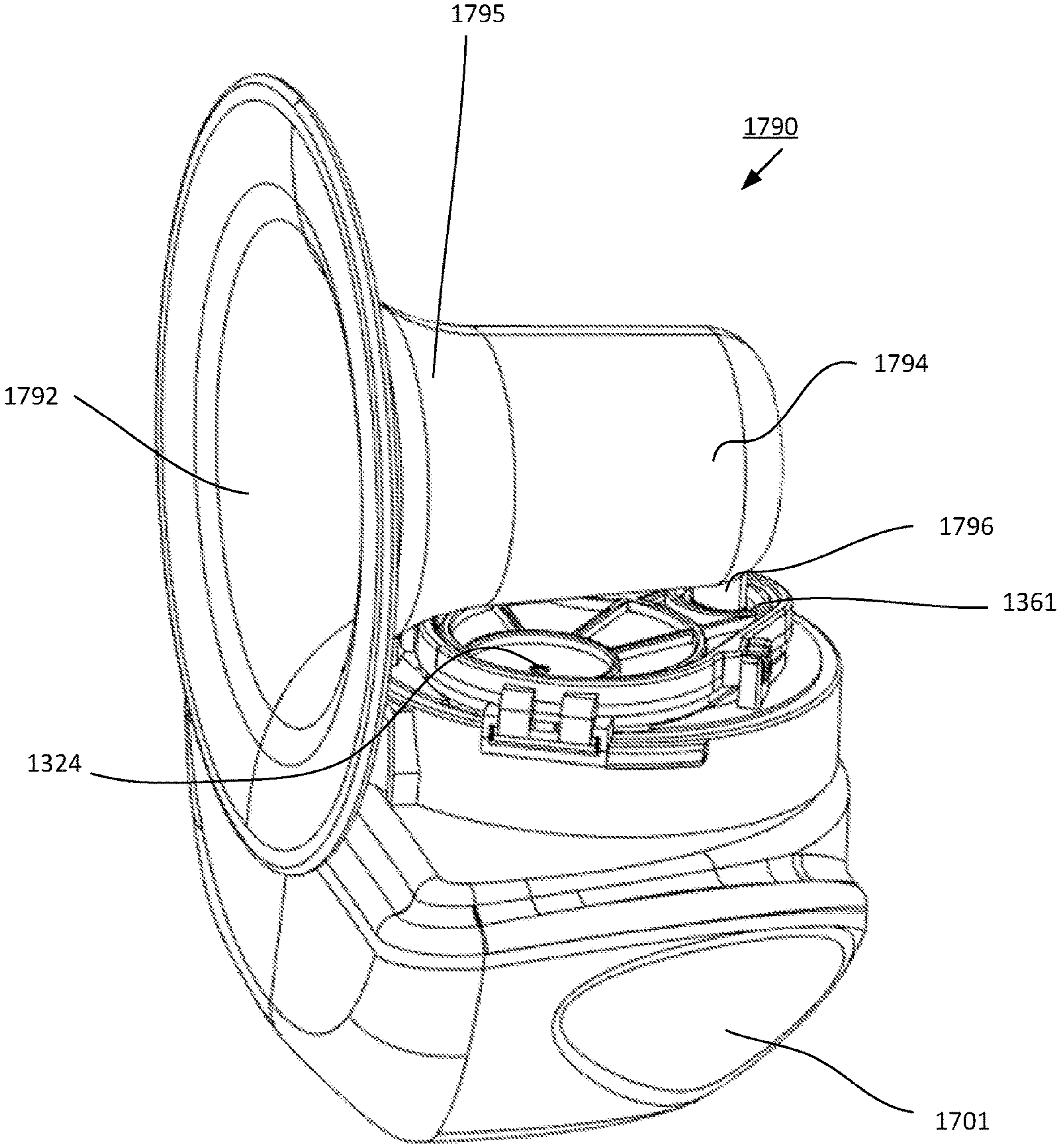
FIG. 17 shows a breast pump including the breast pump valve assembly of FIG. 13.

Referring now to FIG. 17, there is shown a breast pump 1790 suitable for use expressing breastmilk, including the valve assembly 1300 of the example shown in FIGS. 13 to 16.

The breast pump 1790 further includes a breast receiving part 1792 (for example a breast horn), a fluid collection container 1701. The valve assembly 1300 is configured substantially the same as the valve assembly 1300 described above with the fluid chamber 108 defined between the first and second one-way valves 1362, 1364.

The breast receiving part 1792 includes a nipple receiving portion 1794 and a breast contacting portion 1795 configured to engage with a user's breast. The nipple receiving portion 1794 is provided as a substantially cylindrical cup, suitably sized to receive a user's nipple. The breast contacting portion 1792 is provided as a substantially spherical dome, suitably sized to contact the skin around a user's nipple when the nipple is placed inside the nipple receiving portion 1794. A first end of the nipple receiving portion 1794 opens to the centre of the breast contacting portion 1792 to thereby receive the nipple. A second end of the nipple receiving portion 1794 includes an opening 1796 adapted to allow fluid, such as air or expressed milk, to flow out therefrom. The opening 1796 is configured to fluidly couple to the fluid inlet 1361 of the valve assembly, in this example via a connecting tube.

As such, the first one-way valve 1362 is configured to allow flow of fluid (e.g. breast milk) from the nipple receiving part 1794 into the fluid chamber 108 and the second one-way valve 1364 is configured to allow flow of fluid (e.g. breast milk) from the fluid chamber 108 to the fluid collection container 1701. In this way, the fluid flow path is provided from the nipple receiving portion 1794 to the fluid collection container 1701 via the fluid chamber 108 of the valve assembly 1300.

As described above, the valve assembly 1300 includes the suction chamber 104 and the vacuum port 1324. The vacuum port 1324 of the valve assembly 1300 is configured to be fluidly connected to a negative pressure source, for example a reciprocating vacuum pump (not shown). The breast pump 1790 may include the negative pressure source, or in other examples an external negative pressure source may be used, which can be fluidly coupled to the suction chamber via the vacuum port 1324.

The fluid outlet 1722 is fluidly connected to the fluid collection container 1701. The fluid collection container 1701 may be releasably connected to the remaining components of the breast pump 190. As described above, in this example, the lower member 1330 of the valve assembly is configured as a lid for a container and includes a screw ring thread. As such, the valve assembly 1700 may be releasably connected to the fluid container 1701 by screwing the valve assembly onto the opening of the fluid container 1701. It will be appreciated that other fastening mechanisms between the lower member 1330 and the fluid container may be possible, for example snap or friction fit.

Various modifications to the detailed arrangements as described above are possible. For example, the support member may be omitted and the displacement member may be provided as a separate part to the first and/or second one-way valves. In another example, the support member may include the first and second one-way valves and the displacement member may be a separate part. The displacement member may be mounted to the lower member to form the suction chamber and the fluid chamber may be formed by releasably coupling the upper and lower members.

Additionally, or alternatively, one or more of the one-way valves may be separate components, mounted to or within the corresponding fluid inlet or outlet. Although duckbill valves are described, other types of valve may be suitably employed, for example dome valves or slit membrane valves.

Although in the examples described above, the fluid inlet, fluid outlet and vacuum port are positioned in the lower member, one or more of the fluid inlet, fluid outlet and vacuum port may be positioned in other suitable locations. So long as the variable volume fluid chamber is positioned between the first and second one-way valves, the first and second one-way valves and corresponding inlet and outlet may be positioned in any suitable location in the valve assembly.

For example, the fluid inlet may be positioned in the lower member as described with reference to FIGS. 2 to 5, whilst the fluid outlet may be positioned in the upper member or a side region of the housing. Similarly, the vacuum port may be positioned in any location so long as it is in fluid communication with the suction chamber.

Figure 11:
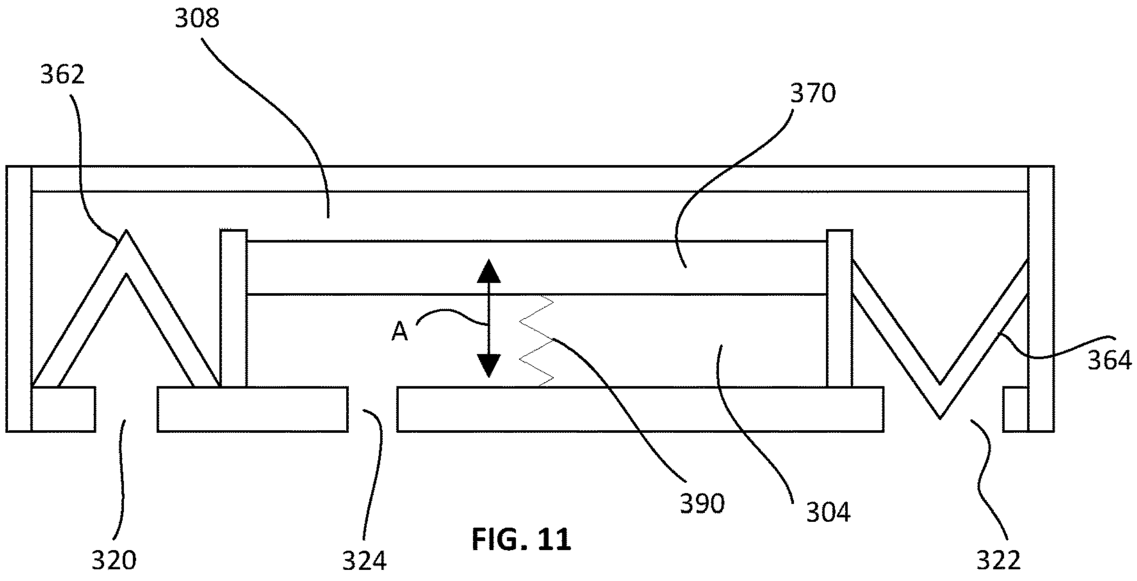
FIG. 11 shows an example of a breast pump valve assembly including an alternative displacement member.

Although the displacement member has been described in the examples above as a diaphragm, the displacement member may be any member suitable for varying the volume of the fluid chamber. For example, the displacement member may include a reciprocating member, which is biased to substantially close the fluid chamber. As shown in FIG. 11, the reciprocating member may be in the form of a piston 370 configured to reciprocate within the fluid chamber 308 in the direction of arrows A. A spring 390, or other suitable biasing element, biases the piston to substantially close the fluid chamber 308.

Upon application of negative pressure to the suction chamber 304 via vacuum port or inlet 324, the piston 370 slides to reduce the volume of the suction chamber 304 and increase the volume of the fluid chamber 308. Pressure in the fluid chamber 308, thereby reduces, opening the first one-way valve 362 to draw fluid into the fluid chamber 308 from the fluid inlet 320.

As negative pressure in the suction chamber 304 is released, the suction chamber returns towards atmospheric pressure and the biasing element 390 acts to move the piston 370 to increase the volume of the suction chamber 304 and decrease the volume of the fluid chamber 308. In doing so, the first one-way valve 362 closes to prevent back flow of fluid and the second one-way valve 364 opens to allow fluid to exit the fluid chamber 308 through the outlet 322. The cycle may then be repeated in the same way as described above with reference to FIGS. 2 to 5.

The reciprocating motion of the piston 370 may alternatively be achieved through manual actuation of a piston rod, for example, mitigating the need for the suction chamber, biasing element and negative pressure source.

Any suitable pump may be used with the breast pump valve assemblies described above including, but not limited to, negative pressure sources such piezoelectric pump, a diaphragm pump, a reciprocating pump, or a peristaltic pump. Alternatively, manually actuated pumps, such as membrane or piston pumps may provide a negative pressure.

Further alternatively, the negative pressure source may be replaced by a device which is actuated either manually or by an electric motor and thereby move the displacement member in order to vary the volume of the fluid chamber. Negative pressure sources as well as actuated devices may be provided in a unit integral with the breast pump valve assembly, or may be provided remote from the breast pump assembly and operably connected via a suitable conduit.

The valve assemblies described herein provide breast pump that advantageously does not release the negative pressure between the breast pump and the user's breast between negative pressure cycles or pulses. The user is thus able to use a breast pump without having to apply pressure to the breast, thereby reducing tiredness and discomfort. Furthermore, there is a reduced risk of breastmilk leaking from the breast pump during expression.

The valve assemblies described herein also provide the advantage that a negative pressure at the nipple is generated using reduced movement of the displacement member. Consequently, the displacement member need only move a small distance when moving from a neutral position to a displaced position, resulting in a valve assembly and a breast pump with reduced size and weight.

The valve assemblies described herein advantageously provide suction with increased efficiency because the suction applied by the breast pump is not repeatedly released and regenerated with every suction cycle. Stimulated expression of breastmilk is provided efficiently and in a continuous manner without interruption.

The breast pump described herein provides improved collection of breastmilk because any fluid drawn into the valve assembly is actively pushed out of the valve assembly outlet to the fluid collection container.

Providing a two-part housing and support member as described above allows for simplified assembly and disassembly of the valve assembly allowing the user to easily clean the valve assembly.

The valve assembly described herein may be compatible with a range of different negative pressure sources or actuating devices. Furthermore, the valve assembly may be used in a variety of breast pump configurations including manual pumps and electric pumps and form part of a wearable or non-wearable breast pump assembly.

It will be clear to a person skilled in the art that features described in relation to any of the embodiments described above can be applicable interchangeably between the different embodiments. The embodiments described above are examples to illustrate various features of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A breast pump valve assembly comprising:

a suction chamber for fluid connection to a negative pressure source;

a fluid chamber defined between a first one-way valve and a second one-way valve, wherein the first one-way valve is configured to allow flow of fluid into the fluid chamber and the second one-way valve is configured to allow flow of fluid out of the fluid chamber; and a displacement member fluidly separating the suction chamber and the fluid chamber, wherein the displacement member is configured such that application of negative pressure to the suction chamber causes movement of the displacement member to thereby increase the volume of the fluid chamber and draw fluid into the fluid chamber through the first one-way valve, wherein the displacement member and first and second one-way valves are integrally formed.

2. A breast pump valve assembly according to claim 1, wherein the displacement member is configured such that, when pressure in the suction chamber is equal to or greater than pressure in the fluid chamber, the displacement member moves to thereby decrease the volume of the fluid chamber and direct fluid in the fluid chamber through the second one-way valve.

3. A breast pump valve assembly according to claim 1, wherein the displacement member is configured to move towards a vacuum port upon application of negative pressure to the suction chamber.

4. A breast pump valve assembly according to claim 1, wherein the displacement member is configured to move between a neutral position when the suction chamber is at atmospheric pressure, and a displaced position when the suction chamber is under negative pressure.

5. A breast pump valve assembly according to claim 4, wherein in the neutral position, the displacement member substantially closes at least a portion of the fluid chamber.

6. A breast pump valve assembly according to claim 1, wherein the displacement member comprises a flexible diaphragm configured to deform upon application of negative pressure to the suction chamber.

7. A breast pump valve assembly according to claim 1, wherein at least one of the displacement member and first and second one-way valves are formed from a fluid impermeable flexible material.

8. A breast pump valve assembly according to claim 7, wherein the flexible material has a Shore-A hardness of from 30 to 70 Shore A.

9. A breast pump valve assembly according to claim 1 wherein the displacement member comprises a reciprocating member biased towards the fluid chamber.

10. A breast pump valve assembly according to claim 1, wherein at least one of the first and second one-way valves is a duck bill valve.

11. A breast pump valve assembly according to claim 1, further comprising a housing comprising a first housing member defining the fluid chamber, and a second housing member defining the suction chamber.

12. A breast pump valve assembly according to claim 11, wherein the displacement member is positioned between the first housing member and the second housing member.

13. A breast pump valve assembly according to claim 11, wherein the first housing member is releasably coupled to the second housing member.

14. A breast pump valve assembly according to claim 11, wherein the first housing member is configured as a lid for coupling to the opening of a fluid container.

15. A breast pump valve assembly according to claim 14, wherein the first housing member comprises a fluid outlet configured to allow flow of fluid from the second one-way valve directly into a fluid container.

16. A breast pump valve assembly according to claim 1, further comprising a fluid inlet, wherein the first one-way valve is configured to allow flow of fluid from the fluid inlet to the fluid chamber.

17. A breast pump valve assembly according to claim 16, further comprising an inlet port for fluidly coupling the inlet to a breast receiving part of a breast pump.

18. A breast pump valve assembly according to claim 1, further comprising a fluid outlet, wherein the second one-way valve is configured to allow flow of fluid from the fluid chamber to the outlet.

19. A breast pump valve assembly according to claim 18, further comprising an outlet port for fluidly coupling the outlet to a fluid collection container.

20. A breast pump valve assembly comprising:

a variable volume fluid chamber defined between a first one-way valve and a second one-way valve, wherein the first one-way valve is configured to allow flow of fluid into the fluid chamber and the second one-way valve is configured to allow flow of fluid out of the fluid chamber; and a displacement member configured for varying the volume of the fluid chamber, wherein the displacement member is configured such that movement of the displacement member to increase the volume of the fluid chamber thereby draws fluid into the fluid chamber through the first one-way valve, wherein the displacement member and first and second one-way valves are integrally formed.

21. A breast pump valve assembly according to claim 20, further comprising a suction chamber, wherein the displacement member fluidly separates the suction chamber and the fluid chamber.

22. A breast pump valve assembly according to claim 21, further comprising a vacuum port for fluidly connecting the suction chamber to a negative pressure source.

23. A breast pump valve assembly according to claim 22, wherein the displacement member is configured such that application of negative pressure to the suction chamber causes movement of the displacement member to thereby increase the volume of the fluid chamber and draw fluid through the first one-way valve into the fluid chamber.

24. A breast pump valve assembly according to claim 20, further comprising an actuator configured to operably move the displacement member to thereby vary the volume of the fluid chamber.

25. A breast pump comprising:

a suction chamber and a vacuum port for fluidly connecting the suction chamber to a negative pressure source;

a breast receiving part, a fluid collection container, and a fluid flow path extending between the breast receiving part and the fluid collection container;

a fluid chamber defined between a first one-way valve and a second one-way valve in the fluid flow path, wherein the first one-way valve is configured to allow flow of fluid from the breast receiving part into the fluid chamber, and the second one-way valve is configured to allow flow of fluid from the fluid chamber to the fluid collection container; and a displacement member fluidly separating the suction chamber and the fluid chamber, wherein the displacement member is configured such that application of negative pressure to the suction chamber causes movement of the displacement member to thereby increase the volume of the fluid chamber and draw fluid from the breast receiving part through the first one-way valve into the fluid chamber, wherein the displacement member and first and second one-way valves are integrally formed.

26. A breast pump according to claim 25, wherein the displacement member is configured such that, increase of pressure in the suction chamber towards atmospheric pressure causes movement of the displacement member to thereby decrease the volume of the fluid chamber and direct fluid in the fluid chamber through the second one-way valve to the fluid collection container.

27. A breast pump according to claim 25, further comprising a negative pressure source fluidly connected to the vacuum port.

28. A breast pump according to claim 27, wherein the negative pressure source is one of: a piezoelectric pump, a diaphragm pump, a reciprocating pump, or a peristaltic pump.

* * * * *